(12) United States Patent
Wu et al.

(10) Patent No.: US 7,153,933 B2
(45) Date of Patent: Dec. 26, 2006

(54) SOLID PHASE METHOD FOR SYNTHESIS PEPTIDE-SPACER-LIPID CONJUGATES, CONJUGATES SYNTHESIZED THEREBY AND TARGETED LIPOSOMES CONTAINING THE SAME

(75) Inventors: Shih-Kwang Wu, Taipei (TW); Ting-Gung Chang, Taipei (TW); Chin-Lu Tseng, Taipei (TW); Li-Jung Chen, Taipei (TW); Kae-Shyang Shih, Taipei (TW)

(73) Assignee: Development Center for Biotechnology, Taipei (TW)

( * ) Notice: Subject to any disclaimer, the term of this patent is extended or adjusted under 35 U.S.C. 154(b) by 135 days.

(21) Appl. No.: 10/308,644

(22) Filed: Dec. 3, 2002

(65) Prior Publication Data

US 2003/0229017 A1 Dec. 11, 2003

Related U.S. Application Data

(63) Continuation-in-part of application No. 10/016,569, filed on Dec. 7, 2001, now abandoned.

(51) Int. Cl.
*C07K 1/04* (2006.01)
*C07K 2/00* (2006.01)
*C07K 1/00* (2006.01)
*C07K 7/64* (2006.01)

(52) U.S. Cl. ............... 530/334; 530/333; 530/300; 530/345; 530/317

(58) Field of Classification Search ........ 530/333–337, 530/345, 402
See application file for complete search history.

(56) References Cited

U.S. PATENT DOCUMENTS

| | | | |
|---|---|---|---|
| 5,451,661 A * | 9/1995 | Wan | 530/345 |
| 5,552,520 A * | 9/1996 | Kim et al. | 530/311 |
| 5,554,728 A * | 9/1996 | Basava et al. | 530/327 |
| 5,565,548 A * | 10/1996 | Neurath et al. | 530/324 |
| 5,804,552 A * | 9/1998 | Basava et al. | 514/7 |
| 5,837,249 A * | 11/1998 | Heber-Katz et al. | 424/186.1 |
| 5,882,645 A * | 3/1999 | Toth et al. | 424/194.1 |
| 5,962,638 A * | 10/1999 | Naumann et al. | 530/329 |
| 6,171,614 B1 * | 1/2001 | Chaikof et al. | 424/450 |
| 6,552,007 B1 * | 4/2003 | Chen et al. | 514/100 |
| 6,610,841 B1 * | 8/2003 | Warren | 536/25.3 |
| 2003/0203038 A1 * | 10/2003 | Vail | 424/490 |

FOREIGN PATENT DOCUMENTS

| | | |
|---|---|---|
| EP | 1 118 336 A2 | 7/2001 |
| WO | 97/31624 | 9/1997 |
| WO | 00/43043 | 7/2000 |

OTHER PUBLICATIONS

H Hojo, et al. Peptide Chemistry (1995) pp. 377-380.*
H Hojo, et al. Tetrahedron Letters (1996) v37, pp. 7391-7394.*
WB Edwards, et al. J. Med. Chem. (1994) v37, pp. 3749-3757.*
Y Han, et al. J. Org. Chem. (1997) v 62, pp. 4307-4312.*
Toth, Istvan., et al., "Novel Lipoamino Acid- and Liposaccharide -Based System for Peptide Delivery: Application for Oral Administration of Tumor Selective Somatostatin Analogues", *Journal of Medical Chemistry*, vol. 42, No. 19, pp. 4010-4013 (1999).
Dasgupta, P., et al., "Lipophilization of Somatostatin Analog RC-160 With Long Chain Fatty Acid Improves its Anti-Proliferative Activity on Human Oral Carcinoma Cells in Vitro", *Life Sciences*, vol. 66, No. 17, pp. 1557-1570 (2000).
Zalipsky, S., et al., "Poly(ethylene glycol)-Grafted Liposomes with Oligopeptide or Oligosaccharide Ligands Appended to the Termini of the Polymer", *Bioconjugate Chemistry*, 1997, vol. 8, pp. 111-118.
Broeckler, C., et al., "Immunogenicity of new heterobifunctional cross-linking reagents used in the conjugation of synthetic peptides to liposomes", *Journal of Immunological Methods*, vol. 191, pp. 1-10.
Verheul, A. F.M., et al., "Monopalmitic acid-peptide conjugates induce cytotoxic T cell responses against malarial epitopes: importance of space amino acids", *Journal of Immunological Methods*, vol. 182 (1995) pp. 219-226.
Hern, D. L., et al., "Incorporation of adhesion peptides into non-adhesive hydrogels useful for tissue resurfacing", Journal of Biomedical Materials Research, vol 39, 1998, pp. 266-276.
Development of ligand-targeted liposomes for cancer therapy : Onocologic, Endocrine & Methods.: Noble, Kirporin, Hayes, Mamot, Hong, Park, Benz, Marks, Drummond: pp. 335-353.
Immunogenicity of new heterobifunctional cross-linking reagents used in the conjugation of synthetic peptides to liposomes: Journal of Immonulogical Methods: Boeckler, Frisch, Muller, Schuber: pp. 1-10.

\* cited by examiner

*Primary Examiner*—Cecilia J. Tsang
*Assistant Examiner*—Andrew D. Kosar
(74) *Attorney, Agent, or Firm*—Ladas and Parry LLP

(57) ABSTRACT

A solid phase synthesis method for preparing peptide-spacer-lipid conjugates, the peptide-spacer-lipid conjugates synthesized by the method, and liposomes containing the peptide-spacer-lipid conjugates. The present invention provides a convenient solid phase synthesis method for preparing peptide-spacer-lipid conjugates and provides various linkage groups (such as amide group) for conjugating peptide, spacer and lipid, wherein the spacer may comprise PEG. Several advantages can be achieved, such as the synthetic procedure can be simplified, the synthesis process can be set to automation, the purification is easier in each reaction step, and the product losses can be reduced to minimal during synthesis. The present synthesis method is suitable for preparing a wide range of peptide-spacer-lipid conjugates, provides a peptide-spacer-lipid conjugate prepared by the solid phase synthesis method of the present invention, which can be incorporated into a liposome as the targeting moiety for liposomal drug delivery to specific cells, and provides a targeting liposome containing the present peptide-spacer-lipid conjugate.

10 Claims, No Drawings

SOLID PHASE METHOD FOR SYNTHESIS PEPTIDE-SPACER-LIPID CONJUGATES, CONJUGATES SYNTHESIZED THEREBY AND TARGETED LIPOSOMES CONTAINING THE SAME

This application is a continuation-in-part application Ser. No. 10/016,569 filed on Dec. 7, 2001, now abandoned.

FIELD OF THE INVENTION

The present invention is related to solid phase synthesis method for preparing peptide-spacer-lipid conjugates and uses of the conjugates.

BACKGROUND OF THE INVENTION

Drug delivery plays a crucial role in the improvement of agents for therapeutic treatment, since many agents have unfavorable drawbacks if they are directly applied to a human body. Therefore, developing a delivery system is necessary for a particular agent to improve its availability such as reduction of side effects, enhancement of efficacy, and convenience in usage. For example, antineoplastic chemotherapies are limited by adverse side effects resulting from their widespread toxicity to normal tissues. Therefore, a delivery system which could prevent drug diffusion and concentrate the drug to the disease site is required.

Liposomes can provide several advantages for use as a drug delivery system for the reasons that they are safe to a biological system, have an excellent spherical bilayer for carrying ether hydrophilic or hydrophobic drugs, and can prevent drugs from degradation and diffusion. Moreover, liposomes can be modified to have additional functions for specific purposes. A successful example is shown as polyethylene-glycerol-grafted (PEG-grafted) liposomes. These modified liposomes can evade the reticuloendothelial system and have prolonged circulation time in blood. Furthermore, cytotoxic cancer drugs encapsulated in the PEG-grafted liposomes provide a remarkable enhancement in anti-tumor activity effect and decrease the side effect of the toxicity to the normal cells. The PEG-grafted liposomes thereby gained commercial application and opened the possibility for further modification of these PEG-grafted liposomes for targeted delivery.

Several types of targeted liposomes have been developed (Maruyama et al., Biochim Biophys Acta. 1995, 1234, 74–80; and Allen T M, Trends Pharmacol Sci. 1994, 15, 215–220). Commonly used targeted liposomes include (1) targeting ligands linked at the lipid headgroups on the conventional liposomes (Type A); (2) targeting ligands linked at the lipid headgroups on the PEG-grafted liposomes (Type B); and (3) targeting ligands attached at the distal end of the PEG chain on the PEG-grafted liposomes (Type C). To date, studies have shown that targeted liposomes of Type C provide a better liposomal structure for targeted delivery (Maruyama et al., Biochim Biophys Acta. 1995, 1234, 74–80). Based on this liposomal structure, several types of molecules, such as antibodies (Ahmad et al., Cancer Res. 1993, 53, 1484–8; and Suzuki et al., Biochim Biophys Acta., 1995, 1245, 9–16), proteins (Eavarone et al., J. Biomed Mater Res. 2000, 51, 10–4) small synthesis molecules (Gabizon et al., Bioconjug Chem. 1999, 10, 289–98) and peptides (Zalipsky et al., Bioconjug Chem. 1997, 8, 111–8), have been developed as the targeting ligands for binding the target sites. Among these types of molecules, peptides are considered as highly potential targeting ligands, since a peptide can serve as a recognition component in protein-protein interactions such as receptor-ligand interactions. Furthermore, many cellular membrane receptors associated with diseases have been studied.

Peptides, such as RGD-peptides, somatostatin, chemotactic peptides, vasoactive intestinal peptide, and mimetics thereof, are good candidates as the targeting ligands. Many counter receptors of these peptides have been found being overexpressed in various tumor cells. Moreover, peptides and peptide mimetics have several unique advantages over other type of molecules (e.g. antibodies). Generally, these peptides bind to target cells with a ligand-receptor association at high affinity and enter the intercellular compartments through receptor-mediate endocytosis. However, an antibody-based targeted liposome may not utilize the endocytosis pathway into the interior of the cells by the antigen on the cell membrane. Furthermore, peptides have less opportunity to be recognized by the reticuloendothelial system and are, thus, cleared from the blood circulation system. Peptide mimetics can provide a higher binding affinity and a better resistance to the proteases degradation than nature peptides.

Currently, two approaches for preparing peptide-based targeted liposomes have been developed, whereby the peptide ligands can be attached at the distal end of PEGs. The first approach is incorporating end-group functionalized PEG-lipid conjugates into liposomes and then conjugating with peptide ligands (Zalipsky et al., Bioconjug. Chem., 1995, 6, 705–8). However, when the end-group functionalized PEGs are conjugated to peptide ligands, a non-homogeneous conjugation may happen if there is more than one reaction group in the peptide ligands. Furthermore, the unreacted end-groups of functionalized PEG are difficult to define and are completely deactivate after the coupling reaction. The second approach is directly incorporating the peptide-PEG-lipid conjugates into liposomal membranes (Zalipsky et al., Bioconjug. Chem., 1997 8, 111–8). This approach can provide a structurally well-defined targeted liposome component.

Although peptide-PEG-lipid conjugates are the expected molecules for preparing the targeted liposomes, the available conjugates are still very limited and the synthesis is difficult. This is so, because, in the peptide-PEG-lipid conjugates, the chemical property of the side chains in peptides is diverse, the molecular mass of PEG is heterogeneous, and the nature of lipids is amphiphilic. These properties cause difficulty in the synthetic processes of side chain protection, purification, and reaction and is evident in that very few peptide-PEG-lipid conjugates have been synthesized and in that the conjugation of a peptide, a spacer, and a lipid often induce the formation of a clumsy linker and an unusual functional group.

Zalipaky et al. (1997) discloses the method for synthesizing YIGSR-PEG-lipid conjugatcs (SEQ ID NO: 1 Tyr-Ile-Gly-Ser-Ary). However, this method cannot be used as a general method for synthesizing a broad range of peptide-PEG-lipid conjugates as a nonspecific reaction of bromoacetyl group with strong nucleophilic residues, such as an amino group or other thiol group, in the peptide may occur. Furthermore, in the YIGSR-PEG-lipid conjugate, a thioacetyl (—S—CH2—CO—) linker was used for conjugating to the peptide and PEG, which is unfavorable in industrialization since an additional modification at the ends of peptide and PEG to a bromoacetyl group and a thiol group, respectively, is required. The urethane linkage between PEG and lipid in the YIGSR-PEG-lipid conjugate is unnatural and acid-base labile. Therefore, a need exists for a synthesis method of preparing a broad range of peptide-spacer-lipid conjugates.

Even though EP 1 118 336 illustrates the synthesis of the Octreotide-spacer-PEG-spacer-DOPE conjugate, the coupling of Octreotide and DOPE by a spacer-PEG-spacer involves four functional groups and three pieces of spacer, which will cause the molecules more complicated and unfavorable for molecule characterization and industrial usages.

BRIEF SUMMARY OF THE INVENTION

The present invention provides a convenient solid phase synthesis method for preparing peptide-PEG-lipid conjugates and provides various linkage groups (such as amide group) for conjugating a peptide, a spacer and a lipid. According to the solid phase synthesis method of the present invention, several advantages can be achieved, such as the simplified synthetic, an automated synthesis, a facile purification process in each reaction step, and minimized product losses during synthesis. In addition, the present synthesis method is suitable for preparing a wide range of peptide-spacer-lipid conjugates.

The present invention also provides a peptide-spacer-lipid conjugate, prepared by the present solid phase synthesis method. The peptide-spacer-lipid can be incorporated into a liposome as the targeting moiety for liposomal drug delivery to specific cells.

The present invention also provides a targeting liposome comprising the present peptide-spacer-lipid conjugate.

ABBREVIATION LIST

The present invention is herein disclosed using the following chemical nomenclature:

| | |
|---|---|
| 2-Br-Cbz | 2-bromobenzyloxycarboyl |
| 2-Br-Z | 2-bromobenzyloxycarbonyl |
| 2-Cl-Cbz | 2-chlorobenzyloxycarboyl |
| 2-Cl-Z | 2-chlorobenzyloxycarbonyl |
| Abu | 4-aminobutyric acid |
| AC | acetyl |
| Acm | acetamidomethyl |
| Boc | t-butyloxycarbonyl |
| Bz | benzoyl |
| Bzl | benzyl |
| Cbz | benzyloxycarboyl |
| DCC | dicyclohexylcarbodiimide |
| DC-Chol | 3β[N-(N',N'-dimethylaminoethane)carbamyl] cholesterol |
| DCM | Dichloromethane |
| DDAB | dimethylammonium bromide |
| Dde | 1-(4,4-dimethyl-2,6-dioxocyclohex-1-ylidene)ethyl |
| DIPCDI | 1,3-diisopropylcarbodiimide |
| DMAP | dimethylaminopyridine |
| DME | ethylene glycol dimethyl ether |
| DMF | N, N-dimethylformamide |
| DMRIE | N-[1-(2,3-ditetradecyloxy)propyl]-N,N-dimethyl-N-hydroxyethylammonium bromide |
| DMS | dimethylsulfide |
| DOPAT | 1,2-dioleyloxy-3-(trimethylamino) propane |
| DOPE | dioleoyl phosphatidylethanolamine |
| DORIE | N-[1-(2,3-dioleoyloxy)propyl]-N,N-dimethyl-N-hydroxy ethylammonium bromide |
| DOTMA | N-[1-(2,3-dioleoyloxy)propyl]-N,N,N-trimethylammonium cholide |
| DOX | doxorubicin |
| DSPE | distearyl phosphatidylethanolamine |
| EDC | 1-(3-dimethylaminopropyl)-3-ethyl-carbodiimide |
| EDT | ethanedithiol |

-continued

| | |
|---|---|
| EGF | epidermal growth factor |
| FGF | fibroblast growth factor |
| Fmoc | 9-fluorenylmethyloxycarbonyl |
| For | formyl |
| HF | hydrogen fluoride |
| HGF | hepatocyte growth factor |
| HOBt | N-hydroxybenzotriazole |
| HSPC | hydrogenated soybean phosphatidylcholine |
| IGF | insulin-like growth factor |
| Im | imidazol-1-yl |
| MBHA | 4-methylbenzhydrylamide |
| MeOH | methanol |
| Mmt | 4-methoxytrityl |
| Mtr | 4-methoxy-2,3,6-trimethylbenzene-sulfonyl |
| Mts | mesitylene-2-sulfonyl |
| Mtt | 4-methlytrityl |
| mPEG-DSPE | methoxypolyethylene glycol-distearyl phosphatidylethanolamine |
| NGF | nerve growth factor |
| NHS | N-hydroxysuccinimide |
| PACAP | pituitary adenylate cyclase-activating peptide |
| Pbf | 2,2,4,6,7-pentamethyldihydro-benzofuran-5-sulfonyl |
| PDGF | platelet-derived growth factor |
| Pd-C | Palladium supported on active carbon catalysts |
| PEG | polyethylene glycol |
| pMeoBzl | p-methoxybenzyl |
| Pmc | 2,2,5,7,8-pentamethylchroman-6-sulfonyl |
| pNP | para-nitrophenyl |
| SPPS | solid phase peptide synthesis |
| SST | somatostatin |
| Su | succinimide |
| TCP | 2,4,5-trichlorophenyl |
| TEA | triethylamine |
| TFA | trifluoroacetic acid |
| TFE | trifluoroethanol |
| TFMSA | trifluoromethanesulfonic acid |
| Tf | trifluoromethanesulfonyl |
| Tfa | trifluoroacetyl |
| TGF | transforming growth factor |
| THP | tetrahydropyranyl |
| Tos | tosyl |
| Trt | trityl |
| tBu | tert-butyl |
| tButhio | tert-butylthio |
| VEGF | vascular endothelial growth factor |
| VIP | vasoactive intestinal peptide |
| Z | benzyloxycarbonyl |

DETAILED DESCRIPTION OF THE INVENTION

I. Solid Phase Synthesis Method for Preparing Peptide-Spacer-Lipid Conjugates

According to the present invention, a solid phase synthesis method for preparing a peptide-PEG-phospholipid conjugate, which comprises the steps of:

(1) synthesizing an amino acid residue protected peptidyl resin in solid phase;

(2) conjugating a PEG and a phospholipid to the peptidyl resin- to form a peptide PEG-phospholipid resin;

(3) cleaving the peptide-PEG-phospholipid resin to obtain a peptide-PEG-phospholipid;

(4) removing at least one side chain protecting group from at least one amino acid of the peptide-PEG-phospholipid, thereby forming a peptide-PEG-phospholipid conjugate; and (5) optionally subjecting the peptide-PEG-phospholipid conjugate to a process selected from the group consisting of: modifying a peptide portion of the peptide-PEG-phospholipid conjugate to a cyclic form after any of the foregoing steps (1)–(4), wherein the PEG is conjugated to each of the peptidyl resin and the phospholipid by a linkage function group, and the linkage functional group is a single amide bond.

A. Solid Phase Synthesis of Amino Acid Residue Protected Peptidyl Resin

The peptidyl resin of the present invention may be prepared by any solid phase synthetic techniques known in the art. The relevant techniques such as Merrifield, *J. Am. Chem. Soc.*, 85, 2149 (1963), Stewart, Solid Phase Peptide Synthesis (Freeman and Co., San Francisco, (1969)), Stewart et al., Solid Phase Peptide Synthesis (Pierce Chemical Company, Rockford, (1984)), and Atherton et al., Solid Phase Peptide Synthesis: A Practical Approach (IRL Press, Oxford (1989)) are incorporated herein by reference in their entirety.

According to the present invention, Fmoc and Boc solid phase peptide synthesis (SPPS) methods are the preferred methods for preparing the peptidyl resin. The Boc SPPS uses an acid-labile Boc (1-butyloxycarbonyl) group as the protecting alpha-amino group, whereas a Fmoc SPPS uses a base-labile Fmoc (9-fluorenylmethyloxycarbonyl) group as the protecting alpha-amino group. The Fmoc and the Boc SPPS are known in the art, for examples, Stewart et al., Solid Phase Peptide Synthesis, Pierce Chemical Company, Rockford (1984), and Chan and White, Fmoc Solid Phase Peptide Synthesis: a Practical Approach, Oxford University Press, Oxford, (2000).

After the initial attachment, the excess reagent and by-product are washed by a washing solution. Subsequent amino acids are added to elongate the peptide chain by the process comprising the steps of: (1) deprotecting the alpha-amino protecting group with a deprotecting reagent; and (2) coupling of the amino acid with a coupling reagent in an organic solvent. A washing step with a washing solution is performed after each deprotecting and coupling step. A Kaiser test (Kaiser et al., *Anal Biochem.* 1970, 34, 595–8) can be used to determine whether the coupling reaction has been completed. The coupling reaction is terminated when the test is "negative." After the desired peptide is completed, the resulting peptidyl resin is then conjugated with a spacer.

According to the present invention, the coupling agent can be selected from the reagents for peptide bond formation. Examples of such coupling reagents include, but not limited to, dicyclohexylcarbodiimide/N-hydroxybenzotriazole (DCC/HOBt), 1,3-diisopropylcarbodiimide/N-hydroxybenzotriazole (DIPCDI/HOBt), and 1-(3-dimethylaminopropyl)-3-ethyl-carbodiimide/N-hydroxysuccinimide (EDC/NHS). A preferred embodiment of the coupling agent is DIPCDI/HOBt.

According to the present invention, the deprotecting agents for a t-butyloxycarbonyl (Boc) protecting group can be trifluoroacetic acid (TFA) and the deprotecting agent for a 9-fluorenylmethyloxycarbonyl (Fmoc) protecting group can be piperidine.

According to the present invention, the primary solvents used for deprotecting, coupling, and washing include, but are not limited to, dichloromethane (DCM) and N,N-dimethylformamide (DMF).

Resins

According to the present invention, various resins can be used for synthesis of peptidyl resin. The resins suitable for Fmoc solid phase peptide synthesis (SPPS) include, but are not limited to, hydroxymethyl resin, Wang resin, 2-Chlorotrityl chloride resin, and Rink amide resin. The resins suitable for Boc SPPS include, but are not limited to, Merrifield resin, 4-methylbenzhydrylamide (MBHA) resin, and oxime resin. The Wang resin and the hydroxymethyl resin can be used for synthesizing the peptides having carboxylic acid (—COOH), alkylamides (—C(O)NHR), di-(alkyl)amides (—C(O)NR$^1$R$^2$) or esters (—C(O)OR) at a C-terminus in the Fmoc chemistry. The Rank amide resin can be used for synthesizing the peptides having an amide (—C(O)NH$_2$) at a C-terminus in the Fmoc chemistry. A 2-Chlorotrityl chloride resin can be used for synthesizing a peptide having carboxylic acid, amine, or hydroxyl functional group at a C-terminus in the Fmoc chemistry. Merrified resins can be used for synthesizing the peptides having a carboxylic acid or esters at a C-terminus in the Boc chemistry. MBHA resins can be used for synthesizing the peptides having an amide at a C-terminus in the Boc chemistry. An oxime resin can be used for synthesizing the peptides having alkylamides or esters at a C-terminus in the Boc chemistry.

In a preferred embodiment of the present invention, the synthesis of a peptide-spacer-lipid conjugate is performed by using a Wang resin, a 2-Chlorotrityl chloride resin, and a Rink amide resin in the Fmoc chemistry.

Amino Protecting Groups

According to the present invention, the amino group in an amino acid, which is used in the peptide chain elongation, can be protected during the amino acid coupling to the elongating peptide. After the coupling reaction, the protecting group is removed for the next amino group-protected amino acid coupling.

According to the present invention, the suitable protecting groups include, but are not limited to, acyl type protecting groups such as formyl, trifluoroacetyl, and acetyl; aromatic urethane type protecting groups such as Fmoc, benzyloxycarboyl (Cbz), and substituted Cbz; aliphatic urethane protecting groups such as t-butyloxycarbonyl (Boc), isopropyloxycarbonyl, and cyclohexyloxycarbonyl; and alkyl type protecting groups such as benzyl and triphenylmethyl. However, the Fmoc and the Boc are the preferred protecting groups.

Side Chain Protecting Groups

According to the present invention, a side chain protecting group is directed to a group which can be attached to the side chain of an amino acid for protecting the side chain during chemical reactions, but which can also be easily removed after the required reactions. The suitable side chain protecting groups for the amino group include, but are not limited to, acetyl (AC), Boc, Cbz, 2-chlorobenzyloxycarboyl (2-Cl-Cbz), 2-bromobenzyloxycarbonyl (2-BrCbz), 4-methlytrityl (Mtt), benzyloxycarbonyl (Z), Fmoc, 1-(4,4-dimethyl-2,6-dioxocyclohex-1-ylidene)ethyl (Dde), and trifluoroacetyl (Tfa). The suitable side chain protecting groups for a hydroxyl group include, but are not limited to, benzyl (Bzl), tert-butyl (tBu), and trityl (Trt). The suitable side chain protecting groups for a thiol group include, but are not limited to, acetamidomethyl (Acm), Bzl, tBu, tert-butylthio (tButhio), p-methoxybenzyl (pMeoBzl), and 4-methoxytrityl (Mmt). The suitable side chain protecting groups for a phenolic hydroxyl group include, but are not limited to, tetrahydropyranyl, tBu, Trt, Bzl, Cbz, z-Br-Cbz, and 2,5-dichlorobenzyl. The suitable side chain protecting groups for an imidazol include, but are not limited to, Boc, Mtt, tosyl (Tos), and Trt. The suitable side chain protecting group for an indole can be, but is not limited to, Boc. The suitable side chain protecting groups for a carboxylic acid include, but are not limited to, benzyl, 2,6-dichlorobenzyl, tBu, and cyclohexyl. The suitable side chain protecting groups for a guanidio group include, but are not limited to, 4-methoxy-2,3,6-trimethylbenzene-sulfonyl (Mtr), mesitylene-2-sulfonyl (Mts), 2,2,4,6,7-pentamethyldihydro-benzofuran-5-sulfonyl (Pbf), 2,2,5,7,8-pentamethylchroman-6-sulfonyl (Pmc), and Tos.

B. The Synthesis of Lipid-Spacer-Peptidyl Resin

In a preferred embodiment of the present invention, the lipid-spacer-peptidyl resin is synthesized by conjugating a spacer to the peptidyl resin to obtain a spacer-peptidyl resin and then conjugating a lipid to the spacer-peptidyl resin.

In another embodiment of the present invention, the lipid-spacer-peptidyl resin is synthesized by conjugating a spacer-lipid to the peptidyl resin.

Conjugation of the Spacer to the Peptidyl Resin

According to the present invention, a hydrophilic polymer spacer can be conjugated to the peptidyl resin through various linkage functional groups. Examples of the linkage functional groups are listed in Table I as follows.

end-group functionalized or activated PEG is shown in the art of Zalipsky S., *Bioconjug. Chem.*, 6, 150–165 (1995).

Conjugation of PEG to the peptidyl-resin requires a suitable functional group at the end of the PEG and the N-terminal of the peptide. When an amine (-peptide-NH-PEG) is the linkage functional group, a PEG with an end-group functionalized by a halide (e.g. —Cl, —Br, and —I) or a sulfonate (e.g. —$OSO_2C_6H_4CH_3$, —$OSO_2CH_2CF_3$) can be used to couple with the amino group at the N-terminal of the peptidyl resin. When a urethane (-peptide-NHC(O)O-PEG) is the linkage functional group, a PEG with an end-group functionalized by an active carbonate (e.g. —C(O)-Im, —OC(O)-pNP, —OC(O)—NHS, —OC(O)-TCP) can be used to couple with the amino group at the N-terminal of the peptidyl resin. When an amide (-peptide-NHC(O)-PEG) is the linkage functional group, a PEG with the end-group functionalized by the

TABLE I

Functional groups of N-terminal of peptides, heads of lipids, and ends of spacers for producing the linkage functional groups

| N-terminal groups of peptides or headgroups of lipids | End groups of spacers | Linkage functional groups |
| --- | --- | --- |
| —$NH_2$ | activated HO—C(=O)—<br>activating agents:<br>DCC/DMAP, DCC/HOBT<br>DIPCDI/HOSu | —NH—C(=O)— |
| —$NH_2$ | X—$CH_2$—<br>X = halide, Tos, Tf | —NH—$CH_2$— |
| —$NH_2$ | R—O—C(=O)—O—<br>R = Im, pNP, Su, TCP | —NH—C(=O)—O— |
| (ketone)—$CH_2$Br | HS—CH₂CH₃ | (ketone)—$CH_2$—S—CH₂CH₃ |
| (ketone)—$CH_2$Br | HS—C(=O)—CH₃ | (ketone)—$CH_2$—S—C(=O)—CH₃ |
| (ketone)—(CH₂)₂—maleimide | HS—CH₂CH₃ | (ketone)—(CH₂)₂—succinimide-S—CH₂CH₃ |

Typically, a linking reaction is performed by coupling an end-group functionalized or activated spacer to the peptidyl resin in a suitable solvent, and shaking at a temperature in a range of approximately 0° C. to approximately 90° C. until the Kaiser test is "negative." After the reaction has been completed, the excess reagents and the by-products are removed by a washing solutions, and then the peptidyl resin is subjected to coupling with the lipid.

In a preferred embodiment of the present invention, the end-group functionalized spacer is a functionalized polyethylene glycol (PEG). A review for the preparation of various activated carboxyl group (e.g., the carboxyl group activated by DCC/HOBt, DCC/dimethylaminopyridine (DMAP), DIPCDI/HOBt, and EDC/NHS) can be used to couple with the amino group at the N-terminal of the peptidyl resin. When a thio ester (-peptide-C(O)$CH_2$SC(O)-PEG) is the linkage functional group, a PEG with the end-group functionalized by the thio acid (-PEG-C(O)S) can be used to couple with the N-terminal of the peptidyl resin in which the N-terminal of the peptidyl resin is modified to bromoacetyl (resin-peptide-C(O)$CH_2$Br). When a thio ether (-peptide-C(O)$CH_2$S$CH_2$-PEG) is the linkage functional group, a PEG with the end-group functionalized by the thiol group (-PEG-CH$_2$SH) can be used to couple with the N-terminal of the peptidyl resin in which the N-terminal of the peptidyl resin is modified to bromoacetyl (resin-peptide-C(O)CH$_2$Br). When the thio ether of a maleimido/thio conjugate is the linkage functional group, a PEG with the end-group functionalized by a thiol group (C(O)-PEG-C(O)CH$_2$CH$_2$SH) can be used to couple with the N-terminal of the peptidyl resin in which the N-terminal of the peptidyl resin is modified to the maleimido group (maleimido-CH$_2$CH$_2$C(O)-peptide-resin).

The suitable solvents for the coupling reaction can be selected from a group consisting essentially of DCM, chloroform, DMF, tetrahydrofuran (THF), and different ratios of mixtures thereof.

The washing solutions can be selected from a group consisting essentially of DCM, chloroform, methanol (MeOH), DMF, THF, CH$_3$CN, water, buffers, and different ratios of mixtures thereof.

In a preferred embodiment of the present invention, the linkage functional group is an amide bond that is a carboxylic group functionalized PEG conjugating to the N-terminal amino group of the peptidyl resin. In the amide bond coupling reaction, the activating agent for carboxyl group in the reaction is selected from a group consisting essentially of the reagents used in peptide bond formation, such as DCC/HOBt, DIPCDI/HOBt or EDC/NHS. The suitable solvents for the coupling reaction are selected from a group consisting essentially of DCM, chloroform, DMF, THF, and different ratios of mixtures thereof. The washing solutions are selected from a group consisting essentially of DCM, chloroform, MeOH, DMF, THF, hydrogen cyanide, water, buffers, and different ratio of mixtures thereof. The reaction temperature is in a range of approximately 20° C. to approximately 90° C. The preferred activating agent for carboxylic group is DIPCDI/HOBt and the solvent is selected from a group consisting essentially of DCM, chloroform and DMF. The preferred washing solutions are selected from a group consisting essentially of chloroform, MeOH, water, DMF, buffers (pH 3.0–11.0), and different ratios of mixtures thereof. The preferred reaction temperature is in a range of approximately 20° C. to approximately 60° C.

Conjugation of Lipid to the Spacer-Peptidyl Resin

According to the present invention, a lipid is conjugated to a spacer-peptidyl resin through linkage functional groups as above described. Typically, the coupling reaction is performed by adding a lipid to an end-group functionalized or activated spacer-peptidyl-resin in a suitable solvent and shaking in a temperature range of approximately 0° C. to approximately 90° C. for a duration of up to approximately 24 hours. After the reaction is completed, the excess reagents and the by-products are removed by washing solutions.

In an embodiment of the present invention, the spacer in a spacer-peptidyl-resin is PEG. Functionalization of the end-group of PEG is above recited with respect to Zalipsky S., Bioconjug. Chem., 6, 150–165 (1995).

Conjugation of a lipid to a spacer-peptidyl-resin requires a suitable functional group at the end of PEG and the headgroup of the lipid. When an amine (lipid-NH-PEG-) is the linkage functional group, a PEG with an end-group functionalized by a halide (e.g. —Cl, —Br, and —I) or sulfonate (e.g., —OSO$_2$C$_6$H$_4$CH$_3$, —OSO$_2$CH$_2$CF$_3$) can be used to couple with the amino group in the headgroup of the lipid. When a urethane (lipid-NHC(O)O-PEG-) is the linkage functional group, a PEG with end-group functionalized by active carbonate (e.g., —C(O)-Im, —OC(O)-pNP, —OC(O)-Su, —OC(O)-TCP) can be used to couple with the amino group in the headgroup of the lipid. When an amide (lipid-NHC(O)-PEG-) is the linkage functional group, a PEG with the end-group functionalized by an activated carboxyl group (e.g., the carboxyl group activated by DCC/HOBt, DCC/DMAP, DIPCDI/HOBt, EDC/NHS) can be used to couple with the amino group in the headgroup of the lipid. When a thio ester (lipid-C(O)CH$_2$SC(O)-PEG-) is the linkage functional group, a PEG with the end-group functionalized by a thio acid (-spacer-C(O)S) can be used to couple with the lipid in which the headgroup is modified to a bromoacetyl (lipid-C(O)CH$_2$Br). When thio ether (lipid-C(O)CH$_2$SCH$_2$-PEG-) is the linkage functional group, a PEG with the end-group functionalized by a thiol group (-spacer-CH$_2$SH) can be used to couple with the lipid in which the headgroup is modified to a bromoacetyl is modified to bromoacetyl (lipid-C(O)CH$_2$Br). When the thio ether of a maleimido/thio conjugate is the linkage functional group, a PEG with the end-group functionalized by a thiol group (-PEG-CH$_2$SH) can be used to couple with the lipid in which the headgroup is attached to a maleimido group (maleimido-CH$_2$CH$_2$C(O)-lipid).

In a preferred embodiment of the invention, the conjugation of a lipid with PEG-peptidyl resin is formed by an amide bond, whereby a carboxylic group at the terminus of the PEG-peptidyl resin is linked to the amino group in the headgroup of the lipid. In general, the coupling reaction initiates by adding an activating agent to activate the end carboxyl group of the carboxyl-PEG-peptidyl resin. A lipid is then added to the activated carboxyl-PEG-peptidyl resin in a suitable solvent with a base, and then the mixture is shaken under nitrogen in a temperature range of approximately 0° C. to approximately 90° C. After the reaction has been completed, the excess reagents and the by-products are removed by washing solutions.

The activating agent for a carboxyl group in the reaction can be selected from a group consisting essentially of the reagents used in peptide bond formation, such as DCC/HOBt, DIPCDI/HOBt, or EDC/HOSu. The suitable solvents for the coupling reaction can be selected from a group consisting essentially of DCM, chloroform, DMF, THF, and different ratios of mixtures thereof. The washing solutions can be selected from a group consisting essentially of DCM, chloroform, MeOH, DMF, THF, CH$_3$CN, water, buffers, and different ratio of mixtures thereof. The reaction temperature is in a temperature range of approximately 20° C. to approximately 90° C. The preferred activating agent for a carboxylic group in the reaction is EDC/NHS. A preferred base in the coupling reaction is triethylamine (TEA). The preferred solvent in the coupling reaction is a mixture of chloroform and DMF. The preferred reaction temperature is in a range of approximately 45° C. to approximately 85° C.

Conjugation of the Spacer-Lipid to the Peptidyl Resin

According to the present invention, the lipid-spacer-peptidyl resin can be synthesized by a process comprising the steps of: (1) preparing an end-group functionalized spacer-lipid conjugate; and (2) coupling the conjugate with the peptidyl resin. The end-group functionalized spacer-lipid conjugate can be synthesized by conjugating an end-group functionalized spacer to a lipid. In one embodiment of the present invention, the end-group functionalized spacer is a functionalized PEG. A review for the preparation of various end-group functionalized or activated PEG can be seen in the art of Zalipsky S., *Bioconjug. Chem.* 6, 150–165 (1995). Examples for synthesizing an end-group functionalized PEG-lipid conjugate is described in Blume et al., *Biochim. Biophys. Acta,* 1149, 180–184 (1993) and Zalipsky *Bioconjugate Chem.,* 4, 269–299 (1993).

According to the present invention, the end-group functionalized PEG-lipid conjugate can be coupled with peptidyl resin following the above described methods.

C. Cleavage of Peptide-Spacer-Lipid from Resin

According to the present invention, cleavage of peptide-spacer-lipid from resin is achieved by shaking a cleavage reagent with a lipid-spacer-peptidyl resin. In general, the cleavage reagents and procedure used in the present invention are the same as the treatment used in the art of SPPS.

When a Wang resin, a 2-Chlorotrityl chloride resin, and a Merrified resin are used to synthesize the peptide-spacer-lipid conjugates with a carboxyl group at a C-terminus, the lipid-spacer-peptidyl resin can be cleaved by a cleavage reagent (a mixture of at least one acid, scavenger, and solvent).

The acid can be selected from a group consisting essentially of TFA, hydrogen fluoride (HF), and trifluoromethanesulfonic acid (TFMSA). The scavenger can be selected from a group consisting essentially of thioanisole, anisole, ethanedithiol (EDT), dimethylsulfide (DMS), ethylmethylsulfide, trifluoroethanol (TFE), 4-methylmercaptophenol, benzyl mercaptan, triethylsilane, and water. The suitable solvents for the cleavage of peptide-spacer-lipid include, but are not limited to, DCM, chloroform, DMF, THF, and different ratios of mixtures thereof. Cleavage of the lipid-spacer-peptide from resin requires a strong acid, such as HF or TFMSA, in the cases of Boc chemistry and TFA in Fmoc chemistry. DCM and DMF are the primary solvents used for cleavage.

When a hydroxymethyl resin or a Wang resin is used to synthesize a lower alkylamide C-terminus of the peptide-spacer-lipid conjugates, cleavage of the peptide-spacer-lipid conjugates from the resin can preferably proceed under a mixture of alkylamine, aluminum chloride, and DCM. The cleavage procedure is known in the art, such as C. R. McArthur, et al., (1982), *Can. J. Chem.,* 60, 1836, which is incorporated herein 778 by reference. When hydroxymethyl resins or Wang resins are used to synthesize a lower alkylated carboxyl C-terminus of peptide-spacer-lipid conjugates, cleavage of the peptide-spacer-lipid conjugates from the resin can preferably proceed under a mixture of alkylalcohol, TEA, potassium cyanide, and benzene. The cleavage procedure is known in the art, such as Moon, et al., (1994), *Tetrahedron Lett.,* 35, 8915, which is incorporated herein by reference. When a Rink amide resin is used to synthesize an amidated carboxyl C-terminus of peptide-spacer-lipid conjugates, cleavage of the peptide-spacer-lipid conjugates from the resin can preferably proceed under a mixture of TFA, scavengers and DCM. When a MBHA resin is used to synthesize an amidated carboxyl C-terminus of peptide-spacer-lipid conjugates, cleavage of the peptide-spacer-lipid conjugates from the resin can preferably proceed under a mixture of HF and scavengers. When an oxime resin is used to synthesize an alkylamide C-terminus of peptide-spacer-lipid conjugates, the cleavage reagent preferably used is $RNH_2$. When an oxime resin is used to synthesize an alkyl ester C-terminus of peptide-spacer-lipid conjugates, the cleavage reagent preferably used is alkylalcohol and TFE.

D. Remove of Side Chain Protecting Groups

In general, the side chain protecting groups in the present invention are removed by the same process used in the art of SPPS. Most side chain protecting groups, such as t-Bu, Boc, Mts, Mmt, Pbf, Pmc, Tos, Trt, of amino acids can be removed by TFA or HF during the cleavage of the peptide-spacer-lipid from the resin. Other side chain protecting groups can be selectively removed by suitable deprotecting agents. The preferred deprotecting agents for removing Acm includes, but are not limited to, Hg(II), Ag(I), Tl(III), and $I_2$. The preferred deprotecting agents for removing Bzl, Z, 2-bromobenzyloxycarbonyl (2-Br-Z), 2-chlorobenzyloxycarbonyl (2-Cl-Z) is palladium (Pd) supported on an active carbon catalysts (Pd-C)/hydrogen gas. The preferred deprotecting agent for removing tButhio includes thio and tributylphosphine. The preferred deprotecting agent for removing Fmoc is piperidine.

E. Modification of the Peptide Portion of the Conjugate

According to the present invention, the peptide portion of a peptide-spacer-lipid conjugate may be modified to a cyclic form by forming an intramolecular linkage between two amino acids or their derivatives in the peptide according to the method known in the art. Examples of the intramolecular linkage include, but not limited to, disulfide, amide, ester, thioether, thioacetate, and thioacetamine, which are shown as follows:

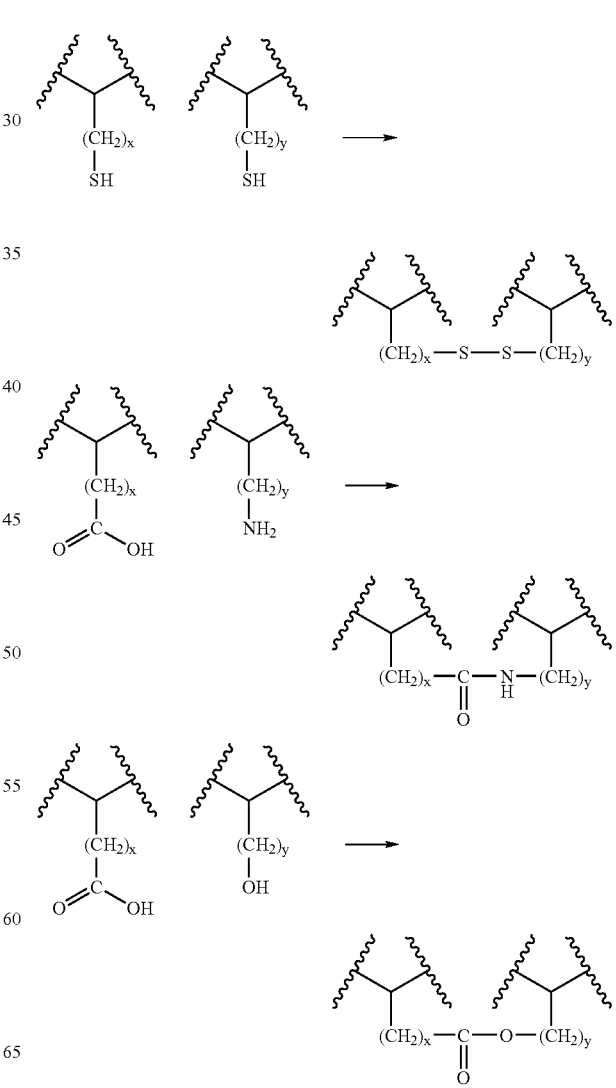

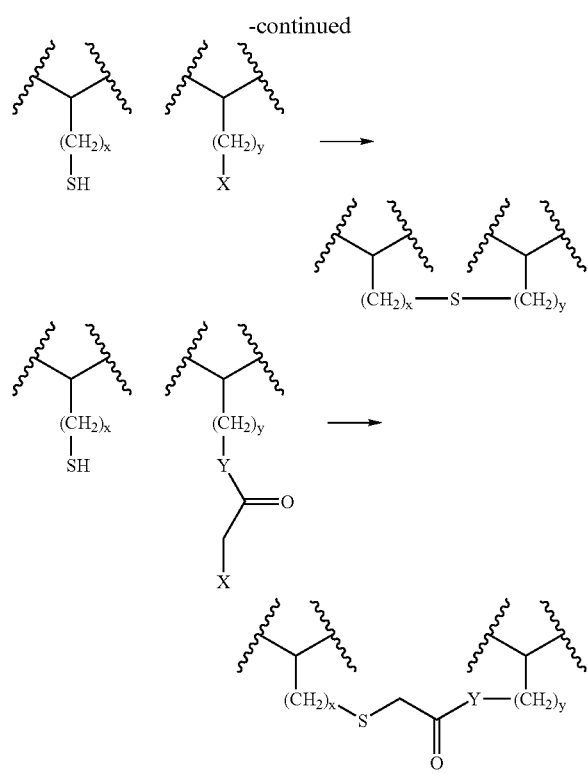

Wherein x and y represent an integer in a range of 1 to 3; X represents either Cl or Br; and Y represents either NH or O.

The intramolecular disulfide bond can be formed by using an oxidizing agent, such as $I_2$, Tl(III), and air, to specifically oxidize the thiol groups in the peptide. The amide and ester bond can be prepared by using carboxyl group activator, such as DCC/HOBt, to form an amide bond with an amino group, or to form an ester bond with a hydroxy group in the peptide. The thioether bond and alpha-substituted acetic acid linkage can be prepared by displacing the chloro or bromo group with a sulfur group. See examples of Englebretsen, D. R. et al., *Tetrahedron Lett.*, 1995, 36, 8871–8874; Barker et al., *J. Med. Chem.*, 1992, 35, 2040–2048; and Or et al., *J. Org. Chem.*, 1991, 56, 3146–3149, each of which is incorporated herein by reference.

F. Purification of the Peptide-Space-Lipid Conjugates

According to the present invention, the method for purifying the peptide-spacer-lipid conjugates includes, but is not limited to, column chromatography, membrane dialysis and combination thereof.

In one embodiment of the present invention, the peptide-spacer-lipid conjugate can be purified by the column chromatography method using gel filtration media. The gel filtration media include, but are not limited to, Sephadex G and LH series, Sepharose series, and Sephacryl series and Superose series.

In another embodiment of the present invention, the peptide-spacer-lipid conjugate can also be purified by the column chromatography method using reversed phase chromatography. The reversed phase chromatography includes, but is not limited to, C8 and C18 series chromatography.

In a further embodiment of the present invention, the aggregated form of the peptide-spacer-lipid conjugate can be isolated from the mixture containing the unwanted components such as peptide-spacer, peptide and other free small molecules by a membrane dialysis. It is preferable that the dialysis membranes have a pore size of molecular weight cut less than 100,000 Dalton.

II. Peptide-Spacer-Lipid Conjugates

According to the present invention, the peptide-spacer-lipid conjugate is synthesized by the present method and is composed of a linear hydrophilic polymer chain having a linkage functional group at each end, which covalently conjugates with a peptide ligand at one end and a lipid at the other end. The peptide-spacer-lipid conjugates can be incorporated into liposomes in which the lipids of the conjugates are inserted into the bilayer of the liposomes to anchor the conjugates in the cell membranes, whereby the peptide ligands of the conjugates facilitate exposure outside of the cell membranes and facilitate selectively binding to cells or tissues.

A. Peptide Ligands

According to the present invention, the peptide ligand is a synthetic peptide composed of natural amino acids. In a preferred embodiment of the present invention, the peptide ligand can bind to a receptor. The receptor can be selected from a group consisting essentially of somatostatin receptors, vasoactive intestinal peptide receptors, integrin receptors, fibroblast growth factor receptors, hepatocyte growth factor receptor, epidermal growth factor receptor, insulin-like growth factor receptor, nerve growth factor receptors, vascular endothelial growth factor receptors, platelet-derived growth factor receptors, and transforming growth factor receptor.

In another embodiment of the present invention, the peptide ligand can be selected from a group consisting essentially of hormones, cytokines, toxins, chemotaxins, and peptides of extracellular matrix for cell adhesion.

Examples of the peptide ligands and ligand-receptor pairs are listed in Table II as follows.

TABLE II

Ligand-receptor pairs and examples of the peptide ligands

| Ligands | Receptor | Examples of Peptide Ligands |
|---|---|---|
| SST | SSTR2, 5 | Octreotide: F(d)-C-F-W(d)-K-T-C-T(ol) |
|  |  | BIM-23268: cyclic C-F-F-W(d)-K-T-F-C-$NH_2$ |
|  |  | BIM-23023: cyclic F(d)-C-Y-W(d)-K-Abu-C-T-$NH_2$ |
| VIP | VIP/PACAP | VIP (1–12): H-S-D-A-V-F-T-D-N-Y-T-R (SEQ ID NO: 2) |
|  |  | EP 0 620 008: A-V-T-T-D-N-Y-T (SEQ ID NO: 3) |
|  |  | Prepro-VIP (111–122): S-S-E-G-E-S-P-O-F-P-E-E-L-E-K (SEQ ID. NO: 4) |
| RGD | integrins | Fibronectin CS-1: E-I-L-D-V (SEQ ID NO: 5) |
|  |  | Fibronectin CS-3: G-R-G-E-S (SEQ ID NO: 6) |
|  |  | Laminin (442–447): L-G-T-I-P-G (SEQ ID NO: 7) |
| HGF | MET | HGF: G-H-K (SEQ ID NO: 8) |
| EGF | EGFR | EGF(20–31): C-M-H-I-E-S-L-D-S-Y-T-C (SEQ ID NO: 9) |
|  | EGFR | U.S. Pat. No. 5,969,099: C-R-F-L-V-Q-D-K-X-A-C (X = aa) (SEQ ID NO: 10) |
| FGF | FGF1R | FGF1(1–11): F-N-L-P-L-G-N-Y-K-K-P (SEQ ID NO: 11) |
|  | FGFR | FGF(119–126): K-R-T-G-Q-Y-K (SEQ ID NO: 12) |
|  |  | WO00/03245: C-S-A-L-F-V-G-A-P-F-H-V-P-D-C (SEQ ID NO: 13) |
|  |  | U.S. Pat. No. 5,789,382: R-K-L-A-V-Y-W-S-S-Y-K-R-SRY (SEQ ID NO: 14) |

TABLE II-continued

Ligand-receptor pairs and examples of the peptide ligands

| Ligands | Receptor | Examples of Peptide Ligands |
|---|---|---|
| IGF | IGFR | IGFI(30–41): G-Y-G-S-S-S-R-R-A-P-Q-T (SEQ ID NO: 15)<br>JP 601009599: Y-F-D-K-P-T-G-Y-G-S-S-S-R-R-A-P-Q-T (SEQ ID NO: 16) |
| NGF | NGFR | Prepro-NGF(99–115): P-E-A-H-W-T-K-L-Q-H-S-L-D-T-A-L-R (SEQ ID NO: 17)<br>W097/15593: C-G-S-E-V-P-N-S-A-R-C-C-V-C (SEQ ID NO: 18) |
| VEGF | VEGFR | C-S-C-K-N-T-D-S-R-C-K-A-G-L-G-L-N-G-R-T (SEQ ID NO: 19) |
| PDGF | PDGFR | G-R-P-R-E-S-G-K-K-R-K-R-K-R-L-K-P-T (SEQ ID NO: 20) |

In another embodiment of the present invention, the peptide ligands are hormones. According to the present invention, the hormones include, but are not limited to, a somatostatin, vasoactive intestinal peptide (VIP), an epidermal growth factor (EGF), a fibroblast growth factor (FGF), a platelet-derived growth factor (PDGF), a nerve growth factor (NGF), a hepatocyte growth factor (HGF), a transforming growth factor (TGF), an insulin-like growth factor (IGF), and a vascular endothelial growth factor (VEGF).

In another preferred embodiment of the present invention, the peptide ligands are peptide fragments of extracellular matrix, which bind to the integrin or laminin receptors. Examples of these peptides include, but are not limited to, the peptides containing the amino acid sequence selected from a group consisting essentially of RGD (SEQ ID NO: 21), RGE (SEQ ID NO: 22), DGEA (SEQ LD NO: 23), EILDV (SEQ ID NO: 24), GPRP (SEQ ID NO: 25), KQAGDV (SEQ ID NO: 26), and QKRLDGS SEQ ID NO: 27).

In another preferred embodiment of the present invention, the peptide ligands are:

EGF(20–31)
  Cys-Met-His-Ile-Glu-Ser-Leu-Asp-Ser-Tyr-Thr-Cys (SEQ ID NO: 9);

FGF I, Acidic Brain Drived (1–11)
  Phe-Asn-Leu-Pro-Leu-Gly-Asn-Tyr-Lys-Lys-Pro (SEQ ID NO: 11);

Laminin Binding Inhibitor (Lamin B-1 (442–447))
  Leu-Gly-Thr-Ile-Pro-Gly (SEQ ID NO: 7);

Integrin Binding Inhibitor (fibronectin CS-3)
  Gly-Arg-Gly-Glu-Ser (SEQ ID NO: 6);

Fibronectin CS-1 (1378–1382)
  Glu-Ile-Leu-Asp-Val (SEQ ID NO: 5);

FGF (119–126)
  Lys-Arg-Thr-Gly-Gln-Tyr-Lys-Leu (SEQ ID NO: 12);

IGF I (30–41)
  Gly-Tyr-Gly-Ser-Ser-Ser-Arg-Arg-Ala-Pro-Gln-Thr (SEQ ID NO: 15);

HGF
  Gly-His-Lys (SEQ ID NO: 8);

Prepro-Nerve Growth Factor (99–15)
  Pro-Glu-Ala-His-Trp-Thr-Lys-Leu-Gln-His-Ser-Leu-Asp-Thr-Ala-Leu-Arg (SEQ ID NO: 17);

Antagonist of Platelet-Derived Growth Factor (PDGF A-Chain 194–211)
  Gly-Arg-Pro-Arg-Glu-Ser-Gly-Lys-Lys-Arg-Lys-Arg-Lys-Arg-Leu-Lys-Pro-Thr (SEQ ID NO: 20);

TGF Alpha (34–43)
  Cys-His-Ser-Gly-Tyr-Val-Gly-Val-Arg-Cys (SEQ ID NO: 28);

VIP (1–12)
  His-Ser-Asp-Ala-Val-Phe-Thr-Asp-Asn-Tyr-Thr-Arg (SEQ ID NO: 2);

VEGF (GST-Exon 7 (1–20))
  Cys-Ser-Cys-Lys-Asn-Thr-Asp-Ser-Arg-Cys-Lys-Ala-Gly-Leu-Gly-Leu-Asn-Gly-Arg-Thr (SEQ ID NO: 19);

Endostatin (Angiogenic Homology Region)
  Ser-Ala-Ala-Ser-Cys-His-His-Ala-Tyr-Ile-Val-Leu-Cys-Ile-Glu-Asn-Ser-Phe-Met-Thr-Ser-Phe-Ser-Lys (SEQ ID NO: 29);

Octreotide (Analogy of Somatostatin)
  Cyclic (D)Phe-Cys-Phe-(D)Trp-Lys-Thr-Cys-Thr(ol).

According to the present invention, the peptide ligands can be peptide mimetics, which are analogues of the peptide ligands defined above containing one or more following modifications:

(1) the amino acid in the peptide is replaced with a non-natural amino acid;

(2) the amino acid in the peptide is replaced with a D form of the natural amino acid;

(3) the C-terminal carboxylic group of the peptide is modified to an amide, a lower alkyl amide, a di-(lower alkyl) amide, a lower ester derivative, a hydroxy, or a lower alkoxy; and (4) the peptide is cyclized.

Amino Acids

According to the present invention, the amino acid is defined as an organic compound containing at least one carboxylic acid group and one amino group. The preferred amino acids include D or L forms of natural amino acids and non-natural amino acids.

The natural amino acids contain 20 alpha-amino acids in which an amino group and a carboxyl group are attached to a carbon. The natural amino acids, having non-polar or hydrophobic side chains, include alanine, valine, leucine, isoleucine, methionine, proline, phenylalanine, and tryptophan; having acidic side chains, include aspartic acid, and glutamic acid; having basic side chains, include lysine, arginine, and histidine; and having uncharged hydrophilic side chains, include asparagine, glutamine, glycine, serine, theronine, tyrosine, and cysteine.

The non-natural amino acids of the present invention include side chain modified amino acids, non-alpha-amino acids, and N-methyl amino acids.

Side chain modified amino acids are alpha-amino acids, wherein the side chain of each amino acid is non-natural or modified from natural amino acid. Examples of side chain modified amino acids include, but are not limited to, 2-aminobutyric acid, 1-aminocyclopropane-1-carboxlic acid, alpha-aminoisobutyric acid, biphenylalanine, p-benzoylphenylalanine, alpha-t-butylglycine, 3-cyclohexylalanine, alpha-cyclohexyglycine, (S)-2,3-diaminopropionic acid, (S)-2,3-diaminobutyric acid, 2-amino-4-phenylbutyric acid, homoserine, homotyrosine, (S)-(−)-indoline-2-carboxylic acid, bata-2-naphthyl alanine, 3-(1-naphthyl)-alanine, 3-(2-naphthyl)-alanine, octahydroindole-2-carboxylic acid, penicillamine, p-aminophenylalanine, 4-bromophenylalanine, 2-chlorophenylalanine, 3-chlorophenylalanine, 3,4-dichlorophenylalanine, 3,4-difluorophenylalanine, 2-fluorophenylalanine, 3-fluorophenylalanine, 4-fluorophenylalanine, 5-hydroxyltryptophan, 4-iodophenylalanine, 4-nitrophenylalanine, pentafluorophenylalanine, pipecolic acid, propargylglycine, thiazolidine-4-carboxylic acid, 1,2,3,4,-tetarhydroisoquinoline-3-carboxylic acid, 3,5-diiodotyrosine, 3-iodotyrosine, 3-nitrotyrosine, O-phosphotyrosine, diethylglycine, di-n-propylglycine, di-n-butylglycine, 1-amino-1-cyclopropane-1-carboxylic acid, 1-amino-1-cyclopentane-carboxylic acid, 1-amino-1-cyclohexane-1-carboxylic acid, and 4-hydroxyproline.

The non-alpha-amino acid is an amino acid whose amino group and carboxyl group are not attached to the same carbon. Examples of the non-alpha-amino acids include, but are not limited to, 2-aminobenzoic acid, 3-aminobenzoic acid, 4-aminobenzoic acid, 4-(aminomethyl)benzoic acid, 4-(aminomethyl)cyclohexane, bata-alanine, gamma-aminobutyric acid, 5-aminovaleric acid, 6-aminohexanoic acid, 8-aminooctanoic acid, 9-aminononanoic acid, 10-aminodecanoic acid, 11-aminoundecanoic acid, 12-aminododecanoic acid, isonipecotic acid, 4-amino-3-hydroxy-6-methylheptanoic acid, 4-amino-5-cyclohexyl-3-hydroxypentanoic acid, and 4-amino-3-hydroxy-5-phenylpentanoic acid.

The N-alkyl amino acid is an amino acid, wherein the alpha-amino group is monoalkylated. The alkyl group includes, but is not limited to, methyl, ethyl, and propyl.

Amino Alcohol

According to the present invention, the amino alcohol is a modified amino acid in which the carboxylic group is modified to a hydroxy group. The amino alcohol can be conjugated to the C-terminus of the peptide chain.

Cyclization of Peptide Ligand

According to the invention, the peptide ligand can be cyclized by forming an intramolecular linkage between two amino acids or their derivatives in the peptide ligands as the above-described methods.

B. Linkage Functional Group

According to the present invention, the linkage functional group is any functional group, which can covalently link the lipid or peptide ligand to the spacer. A variety of functional groups are suitable for use in the peptide-spacer-lipid conjugates, which includes, but are not limited to, those listed in Table I.

C. Spacer Group

According to the present invention, the spacer is a linear hydrophilic polymer chain containing a linkage functional group at each end of the chain for attaching the peptide and lipid. The suitable spacers in the present invention include, but are not limited to, polyglycine, polyethyleneglycol, polypropyleneglycol, polymethacrylamide, polydimethacrylamide, polyhydroxyethylacrylate, polyhydroxypropylmethacrylate, polyoxyalkene and hydrophilic peptides.

In a preferred embodiment of the present invention, the spacer is polyethylene glycol having a molecular weight between 100–10,000 daltons, more preferably between 100–5,000 daltons.

D. Lipid

According to the present invention, the lipid is either a natural or synthetic amphipathic molecule possessing a hydrophilic and a hydrophobic portion on the same molecule, which can spontaneously form bilayer vesicles in water or can be stably incorporated into lipid bilayers.

In an embodiment of the present invention, the lipids are phospholipids including phosphodiglyceride and sphingolipid. The phosphodiglyceride has the structure with a three-carbon glycerol linked to two hydrocarbon chains at 1 and 2 position through an ester or ether linkage and a phosphoryl headgroup at 3 position. The sphingolipid consists of a hydrocarbon chain linked to the nitrogen of sphingosine through an amide bond, which is linked to a phosphoryl headgroup. The phosphoryl headgroup of the phospholipid can be phosphoryl choline, phosphoryl ethanolamine, phosphoryl serine, phosphoryl glycerol, phosphoryl inositol, and phosphatic acid. The hydrocarbon chain in phospholipid, typically, has 14–22 carbon atoms in chain length and can be saturated or at several degrees of unsaturated.

In another preferred embodiment of the present invention, the lipid is distearyl phosphatidylethanolamine (DSPE).

The lipid, which can be stably incorporated into lipid bilayers, includes but is not limited to, stearylamine, dodecylamine, hexadecylamine, acetylpalmitate, glycerol ricinoleate, hexadecyl myristate, isopropyl myristate, amphoteric acrylic polymer, fatty acid amides, cholesterol, cholesterol ester, diacylglycerolsuccinate, diacyl glycerol, fatty acid, and the like.

In another embodiment of the present invention, the lipid is a cationic lipid, which consists of a positively charged headgroup, such as an amine, polyamine, or polylysine, linking to a neutral lipophilic portion, such as a sterol, a hydrocarbon chain, or two hydrocarbon chains. Examples of the cationic lipids include 1,2-dioleyloxy-3-(trimethylamino) propane (DOPAT), N-[1-(2,3-ditetradecyloxy)propyl]-N,N-dimethyl-N-hydroxyethylammonium bromide (DMRIE), N-[1-(2,3-dioleyloxy)propyl]-N,N-dimethyl-N-hydroxy ethylammonium bromide (DORIE), N-[1-(2,3-dioleyloxy)propyl]-N,N,N-trimethylammonium cholide (DOTMA), 3β[N-(N',N'-dimethylaminoethane)carbamoly] cholesterol (DC-Chol), 3β[N-(N',N'-dimethylaminoethane) carbamyl]cholesterol(DC-Chol) and dimethylammonium bromide(DDAB).

III. Targeted Therapeutic Liposomes

The present invention further provides a targeted therapeutic liposome containing the peptide-spacer-lipid conjugates synthesized by the present method.

The targeted therapeutic liposome in the present invention comprises (i) one or more lipids to form liposomal membranes; (ii) one or more peptide-spacer-lipid conjugates incorporated in the liposomal membranes as targeting moieties; (iii) a therapeutic or diagnostic agent incorporated in the liposome; and (iv) optionally, a hydrophilic polymer-lipid conjugate incorporated in the liposome to modify its surface.

A. Components of the Targeted Therapeutic Liposome

Lipids

The suitable lipids for the preparation of liposomes can be one or more lipids selected from a group consisting essentially of the above-defined lipids.

In an embodiment of the present invention, the lipids used in the liposomes include phospholipids and cholesterol. The preferred phospholipid is selected from a group consisting essentially of hydrogenated soybean phosphatidylcholine (HSPC), egg phosphatidylcholine (EPC), and distearyl phosphatidylcholine (DSPC).

In another embodiment of the present invention, the lipids used in the liposomes include lipid and neutral lipid, such as DOPE or cholesterol.

Hydrophilic Polymer-Lipid Conjugates

The surface of the liposome in the present invention can be modified by hydrophilic polymer through incorporating polymer-lipid conjugates into a liposomal bilayer. The polymer-lipid conjugates in the present invention are a linear, hydrophilic polymer chain having repeating units and a linkage functional group attaching to the headgroup of a lipid. Such hydrophilic polymers include, but are not limited to, polyglycine, polyethyleneglycol, polypropyleneglycol, polymethacrylamide, polydimethacrylamide, polyhydroxyethylacrylate, polyhydroxypropylmethacrylate, polyoxyalkene and hydrophilic peptides.

In a preferred embodiment of the present invention, the polymer in polymer-lipid conjugate is PEG having an average molecular weight between 100–10,000 Daltons, more preferably between 100–5,000 Daltons. Monomethoxy or monoethoxy PEG derivatives are also preferred polymers for the lipid conjugates.

Peptide-Spacer-Lipid Conjugates

According to the present invention, the suitable peptide-spacer-lipid conjugates for incorporating into liposomes are one or more peptide-spacer-lipid conjugates synthesized by the above described method.

Therapeutic Agents

Various therapeutic agents, suitable for incorporating into liposomes for use in medical application, are known in the art. However, according to the present invention, the suitable therapeutic agents include, but are not limited to, natural and synthetic compounds having the therapeutic effects of being antineoplastic, anti-angiogenic, anti-bacterial, antiviral, antiparasitic, antifungal, immunoenhancing, immunosuppressive, antimigraine, antipyretic, antisera, anti-inflammatory, anticoagulant, antimetabolic, antidiuretic, antiepileptic, antimitotic, anti-arthritic, anti-arrhythmic, anti-aging, analgesic, anesthetic, hemostatic, hormonal, hormonal suppressing, hypercalcemic alleviating, hypocalcemic alleviating, hyperglycemic alleviating, hypoglycemic alleviating, muscle realxing, neurotransmitting, psychotropic, cardiovascular, thrombolytic, and vasodilating.

According to the present invention, the suitable therapeutic agents for entrapping in the liposomes include, but are not limited to, topoisomerase I and II inhibitors, angiogenesis inhibitors, DNA-transcribing enzyme inhibitors, camptothecin and analogues, antibiotics, antiparasitics, antineoplastics, anti-inflammatory agents, antimetabolites, antimitotic agents, antitumor agents that react or bind with DNA, immune-modifying agents, oligonucleotides and polynucleotides, chemical radiation sensitizers and protectors, and photochemically active anticancer agents.

In a preferred embodiment of the present invention, the incorporated therapeutic agent is a topoisomerase I inhibitor, including but not limited to, camptothecin and analogues that are known in the art as described by Foye W. O. (Cancer Chemotherapeutic Agents, American Chemical Society, Washington, D.C., (1995)).

In another preferred embodiment of the present invention, the incorporated therapeutic agent is an anthracycline that inhibit topoisomerase II. Examples of this kind of drug are doxorubicin, daunorubicin, epirubicin, esorubicin, and idarubicin.

In another preferred embodiment of the present invention, the incorporated therapeutic agent is an antimitotic agent, such as vinblastine, navelbine, vincristine, vinglycinate, vintrypol, and vinzolidine.

In another embodiment of the present invention, the incorporated therapeutic agent is an anti-inflammatory agent.

In another embodiment, the incorporated therapeutic agent is an angiogenesis inhibitor, such as dextrin 2-sulfate, ukrain, thalidomide, angiostatin, endostatin, and 1-[11-(dodecylamino)-10-hydroxyundecyl]-3,7-dimethyl-xanthine.

In another embodiment of the present invention, the incorporated therapeutic agents include nucleic genes, which include, but are not limited to, genes, portions of genes, oligonucleotides, RNA, and analogues thereof. The suitable genes for use as the therapeutic agents include, but are not limited to, (1) tumor suppressor genes, which may compensate for the deficient function of genes by mutation, such as p53, BR1, APC, Rb, DCC, HNPCC, NF-1, NF-2, BRCA1, or BRCA2; (2) toxin genes, which may convert inactive prodrugs into cytotoxic compounds in host cells, such as HSV-tk; (3) immunogenes, which may modify cellular components of the immune system toward a tumor, or modify tumor cells to induce immune response, such as IL-2, IL-4, IL-12, or GM-CSF; (4) genes for chemosensitisation or radiosensitisation, which influence the sensitivity of the cell to chemotherapeutic agents and radiotherapy, such as liver cytochrome P450 gene, CYP2B1, or tk gene; (5) genes or the protein encoded genes, which modulate the apoptotic process of cells, such as TNF/TNFR1, Apo3L/DR3, Apo2L/DR4 or 5, cytochorome c, TP53, E1A, bax, bcl-xs, apoptin, bcl-2, surviving, XIAP, IAP-1, or IAP-2; and (6) genes corresponding to drug resistance, such as MDR1.

The oligonucleotides include, but are not limited to, antisense oligonucleotides, which may bind to mRNA or DNA to regulate translation or transcription of the genes. The target genes of the antisense oligonucleotides include, but are not limited to, mutants of tumor suppressor genes (e.g.,p53, BR1, E1A, and BRCA1); oncogenes (e.g. k-ras, c-myc, and c-fos); genes of growth factors (e.g. IGF 1, PDGF, acidic and basic FGF, and TGFβ); genes encoding the proteins that respond to multiple drug resistance (e.g., MDR1).

Diagnostic Agents

The diagnostic agents used in the present invention include, but are not limited to, gamma emitting radionucleotides for imaging agents in gamma scintigraphy, radiopaque materials for computed tomography, and paramagnetic metal ions for magnetic resonance.

In a preferred embodiment of the present invention, the gamma-emitting radionuclides are 67 Ga, 111 In, and 99 mTc.

In a preferred embodiment of the present invention, the paramagnetic metal ion is Gd.

B. Liposomes

According to the present invention, the liposomes suitable for preparing targeted therapeutic liposomes are spherical particles, which consist of bilayer membranes formed by one or more lipids and one or more aqueous compartments are enclosed therein.

According to the present invention, the liposome size ranges from approximately 30 nm to approximately 1000 nm, depending on the target organs or tissues and the therapeutic agents to be delivered. For example, the preferred liposome size, for a blood stream delivery therapeutic agent, is in a range of approximately 50 nm to approximately 150 nm; and for a directly applied therapeutic agent to tissue or tumor site, the preferred liposome size is in a range of approximately 30 nm to approximately 80 nm.

In a preferred embodiment of the present invention, the liposomes are composed of (1) natural phospholipids that are extracted from soybean or egg, (2) cholesterol, (3) polymer-lipid conjugate.

In another embodiment of the present invention, the liposomes are cationic liposomes including the components of a cationic lipid and one or more neutral lipids, such as DOPE and cholesterol.

C. Preparation of Targeting Therapeutic Liposomes

According to the present invention, the targeted therapeutic liposomes can be prepared by incorporating peptide-spacer-lipid conjugates synthesized by the present method into a therapeutic agent containing liposomes.

The liposomes of the present invention can be prepared by a variety methods as known in the art, for examples, Gregoriadis, G., ed. *Liposome Technology*, Vols., I, II, III, CRC Press, Boca Raton, Fla., 1984; Szoka, F., et al., *Ann. Rev. Biophys. Bioeng.* 9:476 (1980); and New, R.R.C., *Liposomes, a Pratical Approach*, Oxford IRL Press, New York, 1990, which are incorporated herein by reference.

In an embodiment of the present invention, the liposomes are prepared by hydrating a lipid film to produce initial multilamellar vesicles, which are subject to extrusion or homogenization method to reduce the size of the vesicles. Typically, a lipid (or lipid combination) with or without hydrophilic polymer-lipid conjugate in an organic solvent is evaporated and dried in vacuum to form a thin film in a vessel. The lipid film is hydrated in an aqueous solution by vortexing to form the initial multilamellar vesicles. The aqueous vesicles are then performed by several cycles of freezing and thawing. The suspended multilamellar vesicles are downsized by either membrane extrusion or an homogenization method as described in Hope et al, *Biochim. Biophys. Acta.*, 812, 55–65 (1985); Mayhew et al, *Biochim. Biophys. Acta.*, 775, 169–174 (1984); and Brandl et al., in Gregoriadis, G., ed. *Liposome Technology*, 2nd ed., Vol. I, CRC Press, Boca Raton, Fla., 1992, pp. 49–65, which are incorporated herein by reference.

Loading of therapeutic or a diagnostic agent to the liposomes includes the methods of loading water-soluble, hydrophobic and ionic compounds. Water-soluble compounds generally are encapsulated in liposomes by dissolving the agent in an aqueous solution and mixing with a lipid film. Hydrophobic agents can be entrapped into the liposomes or incorporated into the lipid bilayer by dissolving the agent with a lipid or lipid combination in a suitable organic solvent and then evaporating the solvent to produce a thin film. Methods for loading ionic agents can be performed by pH, ionic gradient methods as described in Mayer et al., *Biochemistry*, 27, 2053–2060 (1988) and Haran, G. et al., *Biochim. Biophys. Acta.*, 1151, 201–215 (1993), which are incorporated herein by reference.

DNA can be incorporated to liposomes by several ways, which include, but not limited to, (1) entrapping the DNA into liposomes; (2) forming a lipoplex (a DNA-liposome complex); and (3) forming a lipopolyplex (a complex of liposome, polycationic polymer and DNA). The methods for preparing these DNA incorporated liposomes are known in the art, for examples, Hug P and Sleight R. G., *Biochim. Biophys. Acta.*, 1097:1–17 (1991); Nabel, G. L. et al., Proc. Natl. Acad. Sci. U.S.A., 90, 11307–11311 (1993); Gao, X. and Huang L., *Biochemistry*, 35, 1027–1036 (1996); and Whitmore et al., *Gene Ther.*, 6, 1867–1875 (1999), which are incorporated herein by reference.

According to the present invention, incorporating peptide-spacer-lipid conjugates into liposomal membranes can be achieved by incubating micelles of peptide-spacer-lipid conjugate/methoxypolyethylene glycol-distearyl phosphatidylethanolamine (mPEG-DSPE) with a therapeutic agent-containing liposome at a temperature higher than the transition temperature of the lipid membrane. In general, the dried lipid film of peptide-spacer-lipid conjugate/mPEG-DSPE is hydrated in an aqueous buffer, at a concentration higher than the critical micellar concentration of the conjugates, with gentle swirling of the mixture at a raised temperature. After the lipid film is melted and the mixture becomes a clear micellar solution, the micellar solution is then transferred into the therapeutic agent-containing liposomes at a temperature higher than the transition temperature of the liposomal membrane for a period of time to complete the insertion. The solution is then passed through a size exclusion column to separate micelles and targeted liposomes. Fractions of micelles and targeted liposomes are pooled separately for quantitative analyses.

According to the present invention, the transition temperature of lipid membrane effects the preparation of targeted therapeutic liposomes. The suitable transition temperature of liposomes in the present invention is in a range of approximately 3° C. –approximately 70° C.

The following examples are used for illustration, but not for limiting the present invention.

EXAMPLE 1

Preparation of Amino Alcohol

Preparation of Fmoc-Thr(tBu)-alcohol (Fmoc-Thr(tBu)-ol) Fmoc-Thr(tBu)-OH (1 eq, 0.663 g, 1.67 mmol) was suspended in 2 ml of ethylene glycol dimethyl ether (DME) and chilled below –15° C. under nitrogen. After addition of N-methylmorpholine (1 eq, 0.19 ml, 1.67 mmol) and isobutyl chloroformate (1 eq, 0.22 ml, 1.67 mmol), the mixture was stirred at –15° C. After 5 min of stirring, the precipitate was removed, and a suspension of $NaBH_4$ (3 eq) in 5 ml of water was added and stirred for another 1 hr. At the end of the reaction, 40 ml of water was added. The mixture was extracted with DCM (20 ml×3), and the combined organic layers were washed with 5% $NaHCO_3$, followed by rinsing with brine (e.g., NaCl), and being dried over anhydrous $Na_2SO_4$ (or $MgSO_4$). The solvent was evaporated. Crude Fmoc-Thr (tBu)-alcohol was purified by silica gel column chromatography using DCM as an eluent: 1H-NMR ($CDCl_3$) δ (ppm): 1.16 (3H, d, J=6.2 Hz, CHCH3), 1.20 (9H, s, tBu), 2.88 (1H, broad, OH), 3.61 (1H, broad, CHCH2OH), 3.66 (2H, broad, CHCH2OH), 3.94 (1H, m, CHCH3), 4.22 (1H, t, J=6.8 Hz, CHCH2CO), 4.40 (2H, m, CHCH2CO), 5.28 (1H, d, J=7.5 Hz, NH), 7.30 (2H, d, J=7.4 Hz, aromatics), 7.38 (2H, t, J=7.2 Hz, aromatics), 7.59 (2H, d, J=7.4 Hz, aromatics), 7.74 (2H, d, J=7.4 Hz, aromatics).

EXAMPLE 2

Preparation of Peptidyl-Resins

The peptidyl-resins were prepared according to the Merrified solid phase synthesis techniques (See Steward and Young, Solid Phase Peptide Synthesis, $2^{nd}$ edition, Pierce Chemical Company, Rockford, (1984) and Merrified, *J. Am. Chem. Soc.* 85, 2149–2154 (1963)). In the present invention, a Wang resin, a 2-chlorotrityl chloride resin, and a Rank amide resin in the Fmoc synthetic techniques were used. The Wang resin was used to synthesize the peptidyl moieties in which they have carboxylic acid moiety at a C-terminus. A 2-Chlorotrityl chloride resin was used to synthesize the peptidyl moieties in which they have Pro, Cys, or amino alcohols at a C-terminus. A Rink amide resin was used to synthesize the peptidyl moieties in which they have amide at a C-terminus. Applications of these resins in SPPS were described in the art, for examples, S.-S. Wang, *J. Am. Chem. Soc.*, 95, 1328 (1973) and G. Lu, et al., *J. Org. Chem.*, 46, 3433 (1981) for the Wang resin; K. Barlos, et al., *Int. J. Peptide Protein Res.*, 37, 513 (1991) and K. Barlos, et al., *Int. J. Peptide Protein Res.*, 38, 562 (1991) for 2-Chlorotrityl chloride resin; H. Rink, *Tetrahedron Lett.*, 28, 3787 (1987); M. S. Bematowicz, et al., *Tetrahedron Lett.*, 30, 4645 (1989) for the Rink resin.

The amino groups for peptide chain formation were protected by an Fmoc group. T-butyl was used as the side chain protecting groups for tyrosine, serine, threonine, glutamic acid, and aspartic acid; Trt was used for asparagine and histidine; Boc was used for lysine and tryptophan; Pbf was used for arginine; and Acm was used for cyteine.

In general, the peptides were assembled according to the cycle consisting of (1) 30 min of removing Fmoc protecting group with 20% piperidine-DMF and (2) 2 hr of coupling of the Fmoc amino acid derivative (2 eq) with DIPCDI (2 eq) and HOBt (2 eq) in DMF. The coupling reaction was repeated when the resin became positive to the Kaiser test (Kaiser et al., 1970). After the desired peptide was assembled, a small portion of peptidyl-resin was cleaved by a cleavage cocktail of TFA, chloroform, thioanisole, EDT, and anisole. The cleaved peptide was purified by HPLC and identified by MS. The constructed peptides are listed as below:

EGF
H-Cys(Acm)-Met-His-Ile-Glu-Ser-Leu-Asp-Ser-Tyr-Thr-Cys(Acm)-OH (SEQ ID NO: 9)
MS expected: 1543.7, MS found: 1543.8.

FGF I
H-Phe-Asn-Leu-Pro-Leu-Gly-Asn-Tyr-Lys-Lys-Pro-OH (SEQ ID NO: 11)
MS expected: 1289.7, MS found: 1290.4.

Laminin Binding Inhibitor
H-Leu-Gly-Thr-Ile-Pro-Gly-OH (SEQ ID NO: 7)
MS expected: 556.3, MS found: 557.

Integrin Binding Inhibitor
H-Gly-Arg-Gly-Glu-Ser-OH (SEQ ID NO: 6)
MS expected: 504.2, MS found: 505.

Fibronectin CS-1 Fragment
H-Glu-Ile-Leu-Asp-Val-OH (SEQ ID NO: 5)
MS expected: 587.6, MS found: 587.6.

FGF (119–126)
H-Lys-Arg-Thr-Gly-Gln-Tyr-Lys-Leu-OH (SEQ ID NO: 12)
MS expected: 993.2, MS found: 993.3.

IGF I (30–41)

EXAMPLE 3

Synthesis of End-Group Functionalized PEG Derivatives

Carboxyl-PEG and its active esters

Carboxyl-PEG. $PEG_{2000}$ (8.6 g) and potassium tert-butoxide (20 g) were dissolved in 300 ml tert-butyl alcohol and warmed to 40° C. Ethyl bromoacetate (10 ml) was added over a period of 20 min. The mixture was stirred for 2 hr and then evaporated to remove solvent. The residue was hydrolyzed in 200 ml of 1 N NaOH and stirred at room temperature for 2 hrs. At the end of hydrolysis, the pH of the mixture was adjusted to 2 and extracted by $CHCl_3$ (2×200 ml). The combined extract was washed with water, dried over anhydrous $MgSO_4$, evaporated to concentrate and dried in a vacuum. A white Carboxyl-PEG powder was obtained and yielded 6.88 g. 1H-NMR ($CDCl_3$) δ (ppm): 3.66 (s, O—$CH_2CH_2$—O), 4.13 (s, HO—C(O)—$CH_2$—O).

PEG-oxybenzotriazole HOBt (2.6 mmol), DIPCDI (1.91 mmol), and carboxyl-$PEG_{3000}$ (0.87 mmol) were mixed in 4 ml DMF and stirred at room temperature under nitrogen for 20 min. The mixture was applied to conjugate with peptidyl-resin without further purification of the PEG-oxybenzotriazole.

Activation of carboxyl-PEG with dicyclohexylcarbodiimide (DCC) DMAP (1.91 mmol), DCC (1.91 mmol) and carboxyl-$PEG_{3000}$ (0.87 mmol) were mixed in 4 ml DMF and stirred at room temperature under nitrogen for 20 min. The mixture was applied to conjugate with peptidyl-resin without further purification of the activated carboxyl-PEG.

Succinimidyl ester of carboxyl-PEG (Su-OC(O)-PEG). HNS (2.6 mmol) and EDC (2.6 mmol) were added into a mixture of carboxyl-$PEG_{2000}$ (0.87 mmol) in 4 ml DMF, and stirred at room temperature under nitrogen overnight. At the end of the reaction, the mixture was evaporated to remove the solvent. The residue was added to 10 ml $H_2O$ and extracted with 20 ml DCM for three times. The combined extract was washed with saturated brine (e.g., NaCl), dried over anhydrous $MgSO_4$, and then concentrated and dried in vacuum. The crude product was precipitated by ether and further purified from isopropanol/ether to yield 45%. 1H-NMR ($CDCl_3$) δ (ppm): 2.87 (s, O—N($C(O)CH_2$)$_2$), 3.66 (s, O—$CH_2CH_2$—O), 4.53 (s, —$CH_2$O—C(O)—OSu).

p-Nitrophenyl carbonate of PEG (pNP—O—C(O)-PEG). P-nitrophenyl chloroformate (2.22 g) was added into a mixture of $PEG_{2000}$ (10 g) and TEA (1.31 ml) in 40 ml DCM, and stirred at room temperature under nitrogen overnight. At the end of stirring, the mixture was filtered to removed TEA-HCl salt and evaporated to remove solvent. The crude product was precipitated by isopropyl ether and crystallized from ethyl acetate and ethyl ether twice. 1H-NMR ($CDCl_3$) δ (ppm): 3.66 (s, O—$CH_2CH_2$—O), 3.80 (4H, s, O—$CH_2CH_2$—OC(O)O$C_6H_4NO_2$), 4.44 (4H, s, O—$CH_2CH_2$—OC(O)O$C_6H_4NO_2$), 7.38 & 8.28 (8H, dd, —OC(O)O$C_6H_4NO_2$).

Tos-PEG ($CH_3C_6H_4S(O_2)$O-PEG). P-toluenesulfonyl chloride (2.29 g) was added into a mixture of $PEG_{2000}$ (10 g) and pyridine (1.21 ml) in 15 ml DCM and stirred at room temperature under nitrogen overnight. At the end of the reaction, the mixture was evaporated to remove solvent. A white crude product was precipitated by a mixed solvent of isopropanol/isopropyl ether at 1/1.3 ratio in ice bath. The crude product was crystallized twice by ethyl acetate/ethyl ether at 1/1 volumn ratio. 1H-NMR ($CDCl_3$) δ (ppm): 2.34 (6H, s, —$OSO_2C_6H_4CH_3$), 3.66 (s, O—$CH_2CH_2$—O), 4.15 (4H, s, O—$CH_2CH_2$—$OSO_2C_6H_4CH_3$), 7.16 & 7.79 (8H, dd, —$OSO_2C_6H_4CH_3$).

EXAMPLE 4

Preparation of the Spacer-Lipid Conjugate

Preparation of HOC(O)-$PEG_{2000}$-C(O)NH-DSPE. Su-OC(O)-$PEG_{2000}$ (0.6 mmol) was added to a mixture containing DSPE (0.449 g, 0.6 mmol), TEA (0.2 ml, 1.4 mmol) and DMF (5 ml). The mixture was stirred in a temperature range 40° C. to 45° C. for a duration of 4 hrs. The product was confirmed by thin layer chromatography using a solution of chloroform/methanol/water (3:1:0.1 v/v).

Preparation of Pnp-O-PEG$_{2000}$-C(O)NH-DSPE. pNP-O—C(O)-PEG$_{2000}$ (0.6 mmol) was added to a mixture containing DSPE (0.45 g, 0.6 mmol), TEA (0.6 mmol) and chloroform (10 ml). The mixture was stirred in a temperature range of 40° C. to 45° C. for a duration of approximately 2 hrs. The product was confirmed by thin layer chromatography using a solution of chloroform/methanol/water (3:1:0.1 v/v).

EXAMPLE 5

Conjugation of the Spacer to the Peptidyl Resin

Preparation of HOC(O)-PEG$_{600}$-C(O)NH-(D)Phe-Cys(Acm)-Phe-(D)Trp(Boc)-Lys(Boc)-Thr(tBu)-Cys(Acm)-Thr(tBu)-ol-resin. H-(D)Phe-Cys(Acm)-Phe-(D)Trp(Boc)-Lys(Boc)-Thr(tBu)-Cys(Acm)-Thr(tBu)-ol-resin (0.13 mmol) obtained from solid phase peptide synthesis by 2-chlorotrityl chloride resin was treated with 5 ml of 20% piperidine in DMF to remove the Fmoc protection group from the N-terminus of peptidyl-resin. After removing Fmoc, the resin was washed with DMF (5 ml×3). A mixture of PEG-oxybenzotriazole, obtained by mixing HOBt (0.8 mmol), DIPCDI (0.8 mmol) and carboxyl-PEG$_{600}$ (0.4 mmol) in 5 ml DMF, was added to H-(D)Phe-Cys(Acm)-Phe-(D)Trp(Boc)-Lys(Boc)-Thr(tBu)-Cys(Acm)-Thr(tBu)-ol-resin. The coupling reaction proceeded for 2 hrs at room temperature with shaking. The completion of the reaction was checked by Kaiser test. At the end of the reaction, the excess reagents and byproducts were washed away. A small potion of the HOC(O)-PEG$_{600}$-C(O)NH-(D)Phe-Cys(Acm)-Phe-(D)Trp(Boc)-Lys(Boc)-Thr(tBu)-Cys(Acm)-Thr(tBu)-ol-resin was cleaved and identified by NMR and MS spectroscopy. The 1H NMR (CD$_3$OD) showed ethylene glycol peak at δ 3.5 ppm and the proton of the peptide. In mass spectrum, a bell shape of molecular distribution was observed due to the different molecular mass of PEG. The measured central molecular weight of 1763.5 for HOC(O)-PEG$_{600}$-C(O)NH-(D)Phe-Cys(Acm)-Phe-(D)Trp-Lys-Thr-Cys(Acm)-Thr-ol virtually matches the calculated molecular weight of 1763.6.

Preparation of HOC(O)-PEG$_{2000}$-C(O)NH-(D)Phe-Cys(Acm)-Phe-(D)Trp(Boc)-Lys(Boc)-Thr(tBu)-Cys(Acm)-Thr(tBu)-ol-resin. The reaction conditions and procedures were performed as described above, except that carboxyl-PEG$_{2000}$ was used to replace carboxyl-PEG$_{600}$.

Preparation of HOC(O)-PEG$_{3000}$-C(O)NH-(D)Phe-Cys(Acm)-Phe-(D)Trp(Boc)-Lys(Boc)-Thr(tBu)-Cys(Acm)-Thr(tBu)-ol-resin. The reaction conditions and procedures were performed as described above, except that carboxyl-PEG$_{3000}$ was used to replace carboxyl-PEG$_{600}$.

Preparation of pNP—OC(O)-PEG$_{2000}$-OC(O)NH-(D)Phe-Cys(Acm)-Phe-(D)Trp(Boc)-Lys(Boc)-Thr(tBu)-Cys(Acm)-Thr(tBu)-ol-resin. H-(D)Phe-Cys(Acm)-Phe-(D)Trp(Boc)-Lys(Boc)-Thr(tBu)-Cys(Acm)-Thr(tBu)-ol-resin (0.13 mmol) obtained from solid phase peptide synthesis was treated with 5 ml 20% piperidine in DMF to remove Fmoc protection group from N-terminus of peptidyl-resin. After removing Fmoc, the resin was washed with DMF (5 ml×3). A mixture of pNP—O—C(O)-PEG$_{2000}$ (0.39 mmol) and TEA (1.15 mmol) in 5 ml DMF was added to H-(D)Phe-Cys(Acm)-Phe-(D)Trp(Boc)-Lys(Boc)-Thr(tBu)-Cys(Acm)-Thr(tBu)-ol-resin. The coupling reaction proceeded at room temperature overnight. The completion of the reaction was verified using a Kaiser test. At the end of the reaction, the excess reagents and byproducts were washed away. A small potion of the assembled HO-PEG$_{2000}$-OC(O)NH-(D)Phe-Cys(Acm)-Phe-(D)Trp-Lys-Thr-Cys(Acm)-Thr-ol conjugate was cleaved from the resin and identified by 1H NMR spectroscopy. The 1H NMR (CD$_3$OD) showed ethylene glycol peak at δ 3.5 ppm and the proton of the peptide.

EXAMPLE 6

Conjugation of Lipid to the Spacer-Peptidyl Resin

Preparation of DSPE-NHC(O)-PEG$_{600}$-C(O)NH-(D)Phe-Cys(Acm)-Phe-(D)Trp(Boc)-Lys(Boc)-Thr(tBu)-Cys(Acm)-Thr(tBu)-ol-resin. HOC(O)-PEG$_{600}$-C(O)NH-(D)Phe-Cys(Acm)-Phe-(D)Trp(Boc)-Lys(Boc)-Thr(tBu)-Cys(Acm)-Thr(tBu)-ol-resin (0.13 mmol) in 2 ml DMF was added with NHS (0.4 mmol) and EDC (0.4 mmol) and then the mixture is shaken at room temperature for 4 hrs. Subsequently, DSPE (0.26 mmol) was added to couple with the activated HOC(O)-PEG$_{600}$-C(O)NH-(D)Phe-Cys(Acm)-Phe-(D)Trp(Boc)-Lys(Boc)-Thr(tBu)-Cys(Acm)-Thr(tBu)-ol-resin (0.13 mmol) in a mixed solvent (4 ml chloroform and 0.5 ml TEA) at 55° C. for overnight. After the reaction, the resin was washed with chloroform, DMF, and MeOH and subjected to cleavage.

EXAMPLE 7

Conjugation of Spacer-Lipid to the Peptidyl-Resin

Preparation of DSPE-NHC(O)-PEG$_{2000}$-C(O)NH-(D)Phe-Cys(Acm)-Phe-(D)Trp(Boc)-Lys(Boc)-Thr(tBu)-Cys(Acm)-Thr(tBu)-ol-resin. HOC(O)-PEG$_{2000}$-DSPE (0.4 mmol) in DMF (5 ml) was added DIPCDI (0.8 mmol) and HOBT (0.8 mmol). The solution was stirred at room temperature for 30 min and then added to peptidyl resin. The coupling reaction proceeds for approximately 2 hrs at approximately room temperature with shaking. The completion of the reaction was verified using a Kaiser test. At the end of the reaction, the excess reagents were wash off and the resin was subject to cleavage.

EXAMPLE 8

Cleavage of the Lipid-Spacer-Peptidyl Resin

The DSPE-NHC(O)-PEG$_{600}$-C(O)NH-(D)Phe-Cys(Acm)-Phe-(D)Trp(Boc)-Lys(Boc)-Thr(tBu)-Cys(Acm)-Thr(tBu)-ol-resin was cleaved by a cleavage cocktail (50% TFA, 45% CHCl$_3$, 3.75% anisole, and 1.25% EDT). The cleaved mixture was shaken at room temperature for an additional 10 min to completely remove the protection groups. The mixture was cooled in an ice bath, and then cold ether was added to precipitate the product. The precipitate was spun and washed with cold ether three times. The crude product was purified by liquid chromatography with C8 silica column, and eluted with a methanol gradient (0 to 85% v/v) in water to yield a white solid powder (200 mg/g of resin). The DSPE-NHC(O)-PEG$_{600}$-C(O)NH-(D)Phe-Cys(Acm)-Phe-(D)Trp-Lys-Thr-Cys(Acm)-Thr-ol was identified by 1H NMR and MS. 1H-NMR (MeOH) δ (ppm): 0.90 (6H, t, CH$_3$—(CH$_2$)$_n$—), 1.29 (56H, br. s, —(CH$_2$)$_n$—), 1.97 (6H, s, —NHC(O)—CH$_3$), 1.59 (4H, m, CH$_2$—CH$_2$CH$_2$—C(O)O—), 2.33 (4H, t, —CH$_2$CH$_2$—C(O)O—), 3.63 (268H, s, —O—(CH$_2$CH$_2$)$_n$—O—), 5.23 (1H, s, sn2 proton of glycerol), 6.85–8.50 (15H, aromatic protons of phenyl, indol). The measured central molecular weight of 2451 of the mass spectrum matches the calculated molecular weight of 2450.

EXAMPLE 9

Disulfide Cyclization of Lipid-Spacer-Peptide Conjugate

DSPE-NHC(O)-PEG$_{600}$-C(O)NH-(D)Phe-Cys(Acm)-Phe-(D)Trp-Lys-Thr-Cys(Acm)-Thr-ol was dissolved in methanol at a concentration less than 1.0 mg/ml with 10 equivalent of I$_2$ (40 μl of 20% I$_2$ in 1 ml of methanol) and the mixture is shaken at room temperature for 1 hour. The solution was transferred into a dialysis tube, such as a Spectra/Por™ dialysis tube (MWCO 2,000) and dialyzed against water at 4° C. (3×1000 ml, 8–16 h per period). The solution was then lyophilized to give a white fluffy solid. The measured central molecular weight 2351 of the mass spectrum of cyclized DSPE-NHC(O)-PEG$_{600}$-C(O)NH-(D)Phe-Cys-Phe-(D)Trp-Lys-Thr-Cys-Thr-ol (c-OPD$_{600}$) matches the calculated molecular weight of 2351. 1H-NMR (MeOH) δ (ppm): 0.90 (6H, t, CH$_3$—(CH$_2$)$_n$—), 1.29 (56H, br. s, —(CH$_2$)$_n$—), 1.59 (4H, m, CH$_2$—CH$_2$CH$_2$—C(O)O—), 2.31 (4H, t, —CH$_2$CH$_2$—C(O)O—), 3.64 (268H, s, —O—(CH$_2$CH$_2$)$_n$—O—), 5.22 (1H, s, sn2 proton of glycerol), 6.85–8.50 (15H, aromatic protons of phenyl, indol).

EXAMPLE 10

Additional Synthesis of Peptide-PEG-DSPE Conjugates

Synthesis of cyclo-DSPE-NHC(O)-PEG$_{2000}$-C(O)NH-(D)Phe-Cys-Phe-(D)Trp-Lys-Thr-Cys-Thr-ol (c-OPD$_{2000}$). DSPE-NHC(O)-PEG$_{2000}$-C(O)NH-(D)Phe-Cys(Acm)-Phe-(D)Trp-Lys-Thr-Cys(Acm)-Thr-ol-resin was synthesized by the similar procedure as the synthesis of DSPE-NHC(O)-PEG$_{600}$-C(O)NH-(D)Phe-Cys(Acm)-Phe-(D)Trp-Lys-Thr-Cys(Acm)-Thr-ol-resin. Briefly, the peptidyl-resins were prepared according to the procedure described in example 2. Conjugation of HOC(O)-PEG$_{2000}$-C(O)OH to peptidyl-resins was proceeded by stirring HOBt (0.8 mmol), DIPCDI (0.8 mmol), carboxyl-PEG$_{2000}$ (0.4 mmol) and peptidyl-resins (0.13 mmol) in 5 ml DMF at 45° C. for overnight. After work out the reaction, the HOC(O)-PEG$_{2000}$-C(O)NH-(D)Phe-Cys(Acm)-Phe-(D)Trp(Boc)-Lys(Boc)-Thr(tBu)-Cys(Acm)-Thr(tBu)-ol-resin (0.13 mmol) was activated by NHS (0.4 mmol) and EDC (0.4 mmol) in 2 ml DMF at 55° C. The conjugation of lipid to the PEG-peptidyl resin was performed by adding DSPE to the activated PEG-peptidyl resin (0.13 mmol) in a mixed solvent (4 ml chloroform and 0.2 ml TEA) and heated in 60° C. oil bath for overnight. Cleavage of the conjugate from resin was performed as described in Example 8. The obtained mixture was dissolved in a solvent of methanol/H$_2$O in 1/1 (v/v) ratio and then dialysis through a Spectra/Por membrane (MWCO: 25,000 Dalton) to remove the unwanted components such as peptide-spacer, peptide and other free small molecules. DSPE-NHC(O)-PEG$_{2000}$-C(O)NH-(D)Phe-Cys(Acm)-Phe-(D)Trp-Lys-Thr-Cys(Acm)-Thr-ol was further cyclized by the disulfide bond formation using the process described in Example 9. The cyclized conjugate was purified through Sephadex LH-20 column chromatography and the obtained cyclo-DSPE-NHC(O)-PEG$_{2000}$-C(O)NH-(D)Phe-Cys-Phe-(D)Trp-Lys-Thr-Cys-Thr-ol was structurally confirmed by 1H-NMR (MeOH): δ (ppm): 0.90 (6H, t, CH$_3$—(CH$_2$)$_n$—), 1.29 (56H, br. s, —(CH$_2$)$_n$—), 1.59 (4H, m, CH$_2$—CH$_2$CH$_2$—C(O)O—), 2.32 (4H, t, —CH$_2$CH$_2$—C(O)O—), 3.60 (180H, s, —O—(CH$_2$CH$_2$)$_n$—O—), 5.22 (1H, s, sn2 proton of glycerol), 6.85–8.50 (15H, aromatic protons of phenyl, indol).

Synthesis of cyclo-DSPE-NHC(O)-PEG$_{3000}$-C(O)NH-(D)Phe-Cys-Phe-(D)Trp-Lys-Thr-Cys-Thr-ol (c-OPD$_{3000}$). Cyclo-DSPE-NHC(O)-PEG$_{3000}$-C(O)NH-(D)Phe-Cys-Phe-(D)Trp-Lys-Thr-Cys-Thr-ol was synthesized by the same procedure as cyclo-DSPE-NHC(O)-PEG$_{2000}$-C(O)NH-(D)Phe-Cys-Phe-(D)Trp-Lys-Thr-Cys-Thr-ol, except that the carboxyl-PEG used had an average molecular weight of 3000 Dalton. The obtained cyclo-DSPE-NHC(O)-PEG$_{3000}$-C(O)NH-(D)Phe-Cys-Phe-(D)Trp-Lys-Thr-Cys-Thr-ol had a central molecular weight of about 4600, which matched the calculated average molecular weight.

Synthesis of DSPE-NHC(O)-PEG$_{2000}$-C(O)NH-Gly-Arg-Gly-Asp-Ser-Gly-ol. Peptidyl-resin of Gly-Arg(Pbf)-Gly-Asp(tBu)-Ser(tBu)-Gly-ol-resin was synthesized by using 2-Chlorotrityl chloride resin in Fmoc chemistry as described in Example 2. The following reactions were performed by the same procedure as described in the preparation of DSPE-NHC(O)-PEG$_{2000}$-C(O)NH-(D)Phe-Cys(Acm)-Phe-(D)Trp-Lys-Thr-Cys(Acm)-Thr-ol. The obtained DSPE-NHC(O)-PEG$_{2000}$-C(O)NH-Gly-Arg-Gly-Asp-Ser-Gly-ol showed 1H-NMR (MeOH) δ (ppm): 0.90 (t, CH$_3$—(CH$_2$)$_n$—), 1.29 (br. s, —(CH$_2$)$_n$—1.80 (dd, H on gama-carbon of Arg), 1.93 (m, H on bata-carbon of Arg), 2.32 (t, —CH$_2$CH$_2$—C(O)O—), 2.82 (dd, H on bata-carbon of Asp), 2.92 (dd, H on bata-carbon of Asp), 3.63 (s, —O—(CH$_2$CH$_2$)$_n$—O—), 5.22 (s, sn2 proton of glycerol); the other protons of the alpha carbons and residues in the peptide were distributed in between δ1.5–4.7 ppm,.

Synthesis of DSPE-NHC(O)-PEG$_{2000}$-C(O)NH-Gly-His-Lys-Gly-ol. Peptidyl-resin of Gly-His(Trt)-Lys(Boc)-Gly-ol-resin was synthesized by using 2-Chlorotrityl chloride resin in Fmoc chemistry as described in Example 2. The following reactions were performed by the same procedure as described in the preparation of DSPE-NHC(O)-PEG$_{2000}$-C(O)NH-(D)Phe-Cys(Acm)-Phe-(D)Trp-Lys-Thr-Cys(Acm)-Thr-ol. The obtained DSPE-NHC(O)-PEG$_{2000}$-C(O)NH-Gly-His-Lys-Gly-ol showed 1H-NMR (MeOH) δ (ppm): 0.90 ( t, CH$_3$—(CH$_2$)$_n$—), 1.29 (br. s, —(CH$_2$)$_n$—), 2.32 (4H, t, —CH$_2$CH$_2$—C(O)O—), 3.63 (s, —O—(CH$_2$CH$_2$)$_n$—O—), 5.22 (1H, s, sn2 proton of glycerol); the protons of the alpha carbons and residues in the peptide were distributed in between δ1.5–4.7 ppm.

Synthesis of DSPE-NHC(O)-PEG$_{2000}$-C(O)NH-Cys(Acm)-Met-His-Ile-Glu-Ser-Leu-Asp-Ser-Tyr-Thr-Cys(Acm)-Gly-ol. Peptidyl-resin of Cys(Acm)-Met-His(Trt)-Ile-Gly-Ser(tBu)-Leu-Asp(tBu)-Ser(tBu)-Tyr(tBu)-Thr(tBu)-Cys(Acm)-Gly-ol-resin was synthesized by using 2-Chlorotrityl chloride resin in Fmoc chemistry as described in Example 2. The following reactions were performed by the same procedure as described in the preparation of DSPE-NHC(O)-PEG$_{2000}$-C(O)NH-(D)Phe-Cys(Acm)-Phe-(D)Trp-Lys-Thr-Cys(Acm)-Thr-ol. The obtained DSPE-NHC(O)-PEG$_{2000}$-C(O)NH-Cys(Acm)-Met-His-Ile-Gly-Ser-Leu-Asp-Ser-Tyr-Thr-Cys(Acm)-Gly-ol showed 1H-NMR (MeOH) δ (ppm): 0.90 (t, CH$_3$—(CH$_2$)$_n$—), 1.29 (br. s, —(CH$_2$)$_n$—), 2.32 (t, —CH$_2$CH$_2$—C(O)O—), 3.63 (s, —O—(CH$_2$CH$_2$)$_n$—O—), 5.22 (s, sn2 proton of glycerol); the protons of the alpha carbons and residues in the peptide were distributed in between δ1.5–4.7 ppm; the protons of the aromatic rings in the peptide were distributed in between δ6.5–8.6.

EXAMPLE 11

Preparation of Therapeutic Agent Contained Liposomes

Lipid components of HSPC (0.121 mmol)/Chol/mPEG-DSPE (10:7:0.4 molar ratio) were dissolved in chloroform/ methanol (1:1) and evaporated to remove any organic solvent, and then dried in a vacuum to obtained a lipid film. The lipid film was subjected to a vigorous vortex for hydration in a buffer of 150 mM ammonium sulfate, and a freeze-thaw cycle was proceeded for 10 times. The mixture was extruded through double-stacked polycarbonate membranes (pore sizes from 400 to 100 nm) using an extruding device from Liposofast™ (Ottawa, Canada) to produce liposomes. The outside buffer solution of liposomes was changed to 300 mM histidine by passing through a gel filtration column. Loading of DOX was performed by mixing liposomes with a solution of 10 mg DOX in 1 ml 300 mM histidine at 65° C. for 1 hr. Free DOX was then removed by passing through a gel filtration column in the buffer of HEPES 25 mM and NaCl 150 mM (pH 7.2). The phospholipid concentration of the liposomes was determined by their phosphorus content, the vesicle size was determined by dynamic laser scattering, and DOX content was determined by UV. The liposomes had a mean vesicle size of 135 nm with a standard deviation of <25% and a normal size distribution. The DOX content in the liposomes reaches 0.28 drug/lipid molar ratio.

EXAMPLE 12

Preparation of Targeted Therapeutic Liposomes
DSPE-NHC(O)-$PEG_{600}$-C(O)NH-(D)Phe-Cys-Phe-(D)Trp-Lys-Thr-Cys-Thr-ol/mPEG-DSPE (0.004/0.012 mmol) was dissolved in 3 ml chloroform/methanol (1:1) and evaporated to make a dried lipid film. The dried lipid film was hydrated in 1 ml solution of HEPES 25 mM and NaCl 150 mM (pH 7.2) with gentle swirling of the mixture at 60° C. After the lipid film melted and the mixture turned to a clear micellar solution, the micellar solution was then transferred into 4 ml DOX contained liposomes (contained 0.21 mmol total lipids and 0.058 mmol DOX.HCl) at 60° C. for 4 hours to complete the insertion. The solution is then passed through a gel filtration column, such as Sepharose™ CL-4B (Pharmacia Biotech™) column, to separate micelles and targeted therapeutic liposomes. Fractions of micelles and targeted therapeutic liposomes were pooled separately for quantitative analyses. The inserted peptide-PEG-lipid conjugates in liposomes were about 1% of the total lipid of lipisomes.

EXAMPLE 13

Binding Assay of c-OPD Conjugates with Somatostatin Receptor 2 (SSTR2)
The binding assays of c-$OPD_{600}$ and c-$OPD_{2000}$ conjugates with SSTR2 were preformed according the method as described in Patel, Y. C. and Srikant, C. B., *Endocrinology* 135, 2814–2817 (1994) and Liapakis, G. et al., *J. Biol. Chem.* 271, 20331–20339 (1996). Briefly, cell membranes of CHO—K1 transfected with a plasmid of human somatostatin SSTR2 were used in the binding assays. The binding assay was performed by increasing the concentration of the c-OPD conjugates to compete against the binding of 0.03 nM [$^{125}$I]Somatostatin-14 to the cell membrane. The non-specific binding was defineded as the radioactivity lower than that of 1 μM [$^{125}$I]Somatostatin-14 without the addition of c-OPD conjugates. The binding reaction was proceeded by incubating the cell membranes, [$^{125}$I]Somatostatin-14 and c-OPD conjugate in a buffer containing 25 mM Hepes and 5 mM $MgCl_2$ (pH 7.4) at 25° C. for 4 hours. The binding reaction was terminated by rapidly filtrating through a GF/C glass fiber filter. The filter was then washed with 4 ml of the ice-cold buffer 3 times and then the radioactivity of the bound [$^{125}$I]-Somatostatin-14 was measured. The inhibition constant (Ki) values were calculated by using the equation of Cheng and Prusoff, Cheng, Y. and Prusoff, W. H., *Biochem. Pharmacol.* 22, 3099–3108 (1973). The obtained Ki value for c-$OPD_{600}$ was 25 nM and for c-$OPD_{2000}$ is 11 nM.

Information as herein shown and described in detail is fully capable of attaining the above-described object of the invention, the presently preferred embodiment of the invention, and is, thus, representative of the subject matter, which is broadly contemplated by the present invention. The scope of the present invention fully encompasses other embodiments which may become obvious to those skilled in the art, and is to be limited, accordingly, by nothing other than the appended claims, wherein reference to an element in the singular is not intended to mean "one and only one" unless explicitly so stated, but rather "one or more." All structural, compositional, and functional equivalents to the elements of the above-described preferred embodiment and additional embodiments that are known to those of ordinary skill in the art are hereby expressly incorporated by reference and are intended to be encompassed by the present claims.

Moreover, no requirement exists for a device or method to address each and every problem sought for resolution by the present invention, for such to be encompassed by the present claims. Furthermore, no element, component, or method step in the present disclosure is intended to be dedicated to the public regardless of whether the element, component, or method step is explicitly recited in the claims. However, it should be readily apparent to those of ordinary skill in the art that various changes and modifications in form, reagents, and synthesis detail may be made without departing from the spirit and scope of the inventions as set forth in the appended claims. No claim herein is to construed under the to provisions of 35 U.S.C. §112, sixth paragraph, unless the element is expressly recited using the phrase "means for."

What is claimed is:

1. A solid phase synthesis method for preparing a peptide-PEG-phospholipid conjugate, which comprises the steps of:
   (1) synthesizing an amino acid residue protected peptidyl resin in solid phase;
   (2) conjugating a PEG and a phospholipid to the peptidyl resin to form a peptide-PEG-phospholipid resin;
   (3) cleaving the peptide-PEG-phospholipid resin to obtain a peptide-PEG-phospholipid;
   (4) removing at least one side chain protecting group from at least one amino acid of the peptide-PEG-phospholipid, thereby forming a peptide-PEG-phospholipid conjugate; and
   (5) optionally modifying the peptide portion of the peptide-PEG-phospholipid conjugate to a cyclic form after any of the foregoing steps (1)–(4);
   wherein the PEG is conjugated to each of the peptidyl resin and the phospholipid by a single amide bond.

2. The method of claim 1, where in the peptidyl resin is synthesized by a process selected from the group consisting of Fmoc solid phase peptide synthesis and Boc solid phase peptide synthesis.

3. The method of claim 1, wherein the peptide-PEG-phospholipid resin is formed by conjugating a PEG to the peptidyl resin to obtain a PEG-peptidyl resin and by subsequently conjugating a phospholipid to the PEG-peptidyl resin.

4. The method of claim 1, wherein the peptide-PEG-phospholipid resin is formed by conjugating a PEG-phospholipid to the peptidyl resin.

5. The method of claim 1, wherein the PEG has an average molecular weight in a range of approximately 100 to approximately 10,000 daltons.

6. The method of claim 1, wherein the amide bond is formed by an activating agent selected from the group consisting of dicyclohexylcarbodiimide/N-hydroxybenztriazole (DCC/HOBt), 1,3-diisopropylcarbodiimide/N-hydroxybenztriazole (DIPCDI/HOBt), and 1-(3-dimethylaminopropyl)-3-ethyl-carbodiimide/N-hydroxysuccinimide (EDC/HOSU).

7. The method of claim 1, wherein the amide bond is formed in at least one solvent selected from the group consisting of DCM, $CHCl_3$, DMF and THF.

8. The method of claim 1, wherein the amide bond is formed in a temperature range of approximately 20° C. to approximately 90° C.

9. The method of claim 1, wherein the cyclic form of the peptide portion is formed by an intramolecular linkage between a pair of components selected from the group consisting of two amino acids and at least one derivative of two amino acids.

10. The method of claim 9, wherein the intramolecular linkage is selected from the group consisting of disulfide, amide, ester, thioether, thioacetate, and thioacetamine.

\* \* \* \* \*

SEQUENCE LISTING

<160> NUMBER OF SEQ ID NOS: 29

<210> SEQ ID NO 1
<211> LENGTH: 5
<212> TYPE: PRT
<213> ORGANISM: Human Cell

<400> SEQUENCE: 1

Tyr Ile Gly Ser Arg
1               5

<210> SEQ ID NO 2
<211> LENGTH: 12
<212> TYPE: PRT
<213> ORGANISM: Human Cell

<400> SEQUENCE: 2

His Ser Asp Ala Val Phe Thr Asp Asn Tyr Thr Arg
1               5                   10

<210> SEQ ID NO 3
<211> LENGTH: 8
<212> TYPE: PRT
<213> ORGANISM: Human Cell

<400> SEQUENCE: 3

Ala Val Thr Thr Asp Asn Tyr Thr
1               5

<210> SEQ ID NO 4
<211> LENGTH: 15
<212> TYPE: PRT
<213> ORGANISM: Human Cell

<400> SEQUENCE: 4

Ser Ser Glu Gly Glu Ser Pro Gln Phe Pro Glu Glu Leu Glu Lys
1               5                   10                  15

<210> SEQ ID NO 5
<211> LENGTH: 5
<212> TYPE: PRT
<213> ORGANISM: Human Cell

<400> SEQUENCE: 5

Glu Ile Leu Asp Val
1               5

<210> SEQ ID NO 6
<211> LENGTH: 5
<212> TYPE: PRT
<213> ORGANISM: Human Cell

<400> SEQUENCE: 6

Gly Arg Gly Glu Ser
1               5

<210> SEQ ID NO 7
<211> LENGTH: 6
<212> TYPE: PRT
<213> ORGANISM: Human Cell

<400> SEQUENCE: 7

Leu Gly Thr Ile Pro Gly
1               5

<210> SEQ ID NO 8
<211> LENGTH: 3
<212> TYPE: PRT
<213> ORGANISM: Human Cell

<400> SEQUENCE: 8

Gly His Lys
1

<210> SEQ ID NO 9
<211> LENGTH: 12

```
<212> TYPE: PRT
<213> ORGANISM: Human Cell

<400> SEQUENCE: 9

Cys Met His Ile Glu Ser Leu Asp Ser Tyr Thr Cys
1               5                   10

<210> SEQ ID NO 10
<211> LENGTH: 11
<212> TYPE: PRT
<213> ORGANISM: Human Cell
<220> FEATURE:
<221> NAME/KEY: MISC_FEATURE
<222> LOCATION: (9)..(9)
<223> OTHER INFORMATION: Unknown or Other

<400> SEQUENCE: 10

Cys Arg Phe Leu Val Gln Asp Lys Xaa Ala Cys
1               5                   10

<210> SEQ ID NO 11
<211> LENGTH: 11
<212> TYPE: PRT
<213> ORGANISM: Human Cell

<400> SEQUENCE: 11

Phe Asn Leu Pro Leu Gly Asn Tyr Lys Lys Pro
1               5                   10

<210> SEQ ID NO 12
<211> LENGTH: 8
<212> TYPE: PRT
<213> ORGANISM: Human Cell

<400> SEQUENCE: 12

Lys Arg Thr Gly Gln Tyr Lys Leu
1               5

<210> SEQ ID NO 13
<211> LENGTH: 15
<212> TYPE: PRT
<213> ORGANISM: Human Cell

<400> SEQUENCE: 13

Cys Ser Ala Leu Phe Val Gly Ala Pro Phe His Val Pro Asp Cys
1               5                   10                  15

<210> SEQ ID NO 14
<211> LENGTH: 15
<212> TYPE: PRT
<213> ORGANISM: Human Cell

<400> SEQUENCE: 14

Arg Lys Leu Ala Val Tyr Trp Ser Ser Tyr Lys Arg Ser Arg Tyr
1               5                   10                  15

<210> SEQ ID NO 15
<211> LENGTH: 12
<212> TYPE: PRT
<213> ORGANISM: Human Cell

<400> SEQUENCE: 15

Gly Tyr Gly Ser Ser Ser Arg Arg Ala Pro Gln Thr
1               5                   10
```

```
<210> SEQ ID NO 16
<211> LENGTH: 18
<212> TYPE: PRT
<213> ORGANISM: Human Cell

<400> SEQUENCE: 16

Tyr Phe Asp Lys Pro Thr Gly Tyr Gly Ser Ser Arg Arg Ala Pro
1               5                   10                  15

Gln Thr

<210> SEQ ID NO 17
<211> LENGTH: 17
<212> TYPE: PRT
<213> ORGANISM: Human Cell

<400> SEQUENCE: 17

Pro Glu Ala His Trp Thr Lys Leu Gln His Ser Leu Asp Thr Ala Leu
1               5                   10                  15

Arg

<210> SEQ ID NO 18
<211> LENGTH: 14
<212> TYPE: PRT
<213> ORGANISM: Human Cell

<400> SEQUENCE: 18

Cys Gly Ser Glu Val Pro Asn Ser Ala Arg Cys Cys Val Cys
1               5                   10

<210> SEQ ID NO 19
<211> LENGTH: 20
<212> TYPE: PRT
<213> ORGANISM: Human Cell

<400> SEQUENCE: 19

Cys Ser Cys Lys Asn Thr Asp Ser Arg Cys Lys Ala Gly Leu Gly Leu
1               5                   10                  15

Asn Gly Arg Thr
            20

<210> SEQ ID NO 20
<211> LENGTH: 18
<212> TYPE: PRT
<213> ORGANISM: Human Cell

<400> SEQUENCE: 20

Gly Arg Pro Arg Glu Ser Gly Lys Lys Arg Lys Arg Lys Arg Leu Lys
1               5                   10                  15

Pro Thr

<210> SEQ ID NO 21
<211> LENGTH: 3
<212> TYPE: PRT
<213> ORGANISM: Human Cell

<400> SEQUENCE: 21

Arg Gly Asp
1

<210> SEQ ID NO 22
<211> LENGTH: 3
<212> TYPE: PRT
<213> ORGANISM: Human Cell
```

-continued

```
<400> SEQUENCE: 22

Arg Gly Glu
1

<210> SEQ ID NO 23
<211> LENGTH: 4
<212> TYPE: PRT
<213> ORGANISM: Human Cell

<400> SEQUENCE: 23

Asp Gly Glu Ala
1

<210> SEQ ID NO 24
<211> LENGTH: 5
<212> TYPE: PRT
<213> ORGANISM: Human Cell

<400> SEQUENCE: 24

Glu Ile Leu Asp Val
1               5

<210> SEQ ID NO 25
<211> LENGTH: 4
<212> TYPE: PRT
<213> ORGANISM: Human Cell

<400> SEQUENCE: 25

Gly Pro Arg Pro
1

<210> SEQ ID NO 26
<211> LENGTH: 6
<212> TYPE: PRT
<213> ORGANISM: Human Cell

<400> SEQUENCE: 26

Lys Gln Ala Gly Asp Val
1               5

<210> SEQ ID NO 27
<211> LENGTH: 7
<212> TYPE: PRT
<213> ORGANISM: Human Cell

<400> SEQUENCE: 27

Gln Lys Arg Leu Asp Gly Ser
1               5

<210> SEQ ID NO 28
<211> LENGTH: 10
<212> TYPE: PRT
<213> ORGANISM: Human Cell

<400> SEQUENCE: 28

Cys His Ser Gly Tyr Val Gly Val Arg Cys
1               5                   10

<210> SEQ ID NO 29
<211> LENGTH: 24
<212> TYPE: PRT
<213> ORGANISM: Human Cell

<400> SEQUENCE: 29
```

```
-continued

Ser Ala Ala Ser Cys His His Ala Tyr Ile Val Leu Cys Ile Glu Asn
1               5                   10                  15

Ser Phe Met Thr Ser Phe Ser Lys
                20
```